US010865376B2

(12) United States Patent
Drazek et al.

(10) Patent No.: US 10,865,376 B2
(45) Date of Patent: Dec. 15, 2020

(54) METHOD FOR DETECTING THE PRESENCE OR ABSENCE OF BIOLOGICAL PARTICLES

(71) Applicant: bioMérieux, Marcy l'Etoile (FR)

(72) Inventors: Laurent Drazek, Grenoble (FR); Frédéric Pinston, Grenoble (FR)

(73) Assignee: BIOMERIEUX, Marcy l'Etoile (FR)

( * ) Notice: Subject to any disclaimer, the term of this patent is extended or adjusted under 35 U.S.C. 154(b) by 10 days.

(21) Appl. No.: 15/319,643

(22) PCT Filed: Jun. 29, 2015

(86) PCT No.: PCT/FR2015/051763
§ 371 (c)(1),
(2) Date: Dec. 16, 2016

(87) PCT Pub. No.: WO2016/001555
PCT Pub. Date: Jan. 7, 2016

(65) Prior Publication Data
US 2017/0137772 A1   May 18, 2017

(30) Foreign Application Priority Data

Jun. 30, 2014 (FR) .................................... 14 56117

(51) Int. Cl.
*C12M 1/34* (2006.01)
*C12M 1/00* (2006.01)
*C12Q 1/04* (2006.01)
*C12Q 1/18* (2006.01)

(52) U.S. Cl.
CPC ............ *C12M 41/36* (2013.01); *C12M 31/00* (2013.01); *C12M 41/46* (2013.01); *C12Q 1/04* (2013.01); *C12Q 1/18* (2013.01)

(58) Field of Classification Search
None
See application file for complete search history.

(56) References Cited

U.S. PATENT DOCUMENTS

| 4,701,850 | A | 10/1987 | Gibbs |
| 6,107,054 | A | 8/2000 | Gibbs |
| 6,153,400 | A | 11/2000 | Matsumura et al. |
| 6,238,879 | B1 | 5/2001 | Gibbs |
| 6,665,429 | B1 | 12/2003 | Wang |
| 8,855,397 | B2 * | 10/2014 | Moy ........................ C12Q 1/04 382/133 |
| 2003/0186350 | A1 * | 10/2003 | Newell .................... C12Q 1/18 435/32 |
| 2010/0099137 | A1 | 4/2010 | Taintor |
| 2013/0084598 | A1 | 4/2013 | Moy et al. |

FOREIGN PATENT DOCUMENTS

| DE | 20 2004 000 946 U1 | 4/2004 |
| EP | 0 207 739 A2 | 1/1987 |
| EP | 1 016 707 A2 | 7/2000 |
| EP | 1 195 430 A1 | 4/2002 |
| FR | 2 958 298 A1 | 10/2011 |
| WO | 00/55357 A1 | 9/2000 |
| WO | 2011/125033 A1 | 10/2011 |

OTHER PUBLICATIONS

Sep. 16, 2015 Search Report issued in International Patent Application No. PCT/FR2015/051763.
Jan. 3, 2017 International Preliminary Report on Patentability issued in International Patent Application No. PCT/FR2015/051763.

* cited by examiner

*Primary Examiner* — Nghi V Nguyen
(74) *Attorney, Agent, or Firm* — Oliff PLC

(57) ABSTRACT

A method detects the presence or absence of at least one first inhibition zone having a culture of biological particles on a culture medium in the presence of a chemical agent. The method of detection has a first step of seeding the culture medium with the biological particles, a second step in which the culture medium receives the chemical agent, a third step of incubation of the culture medium, and a fourth step of measurement of the first inhibition zone of the culture medium, which includes a first phase of taking an image of the first inhibition zone by ombroscopy.

13 Claims, 24 Drawing Sheets

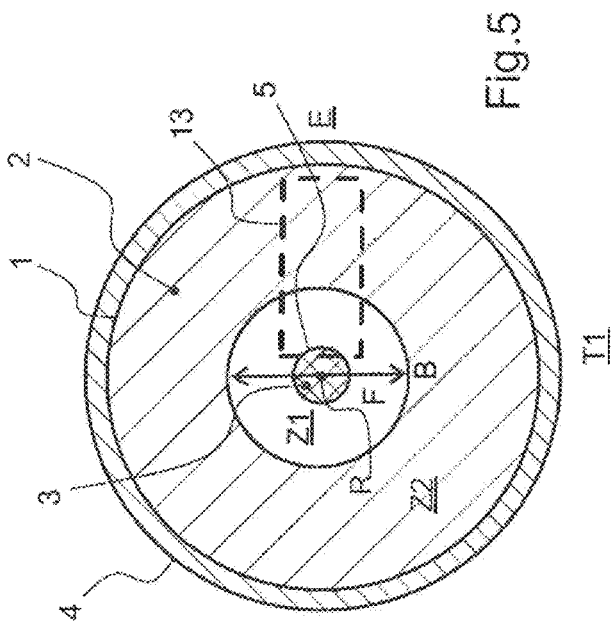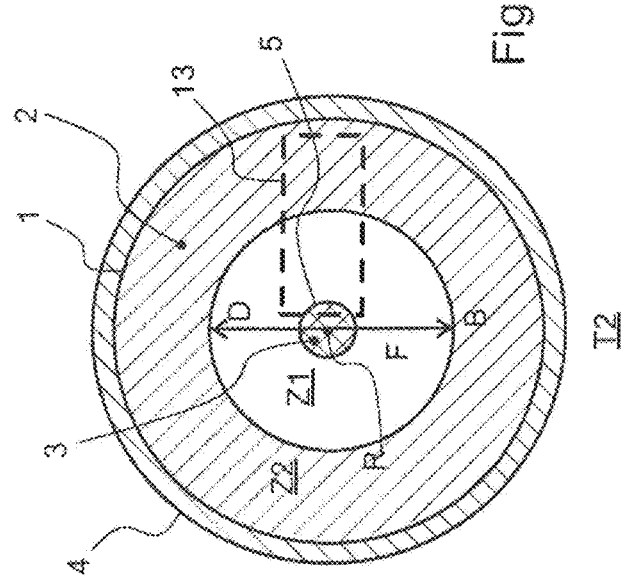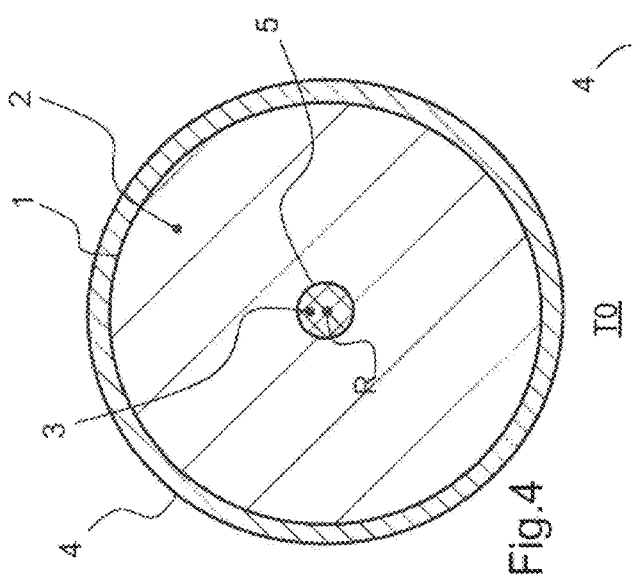

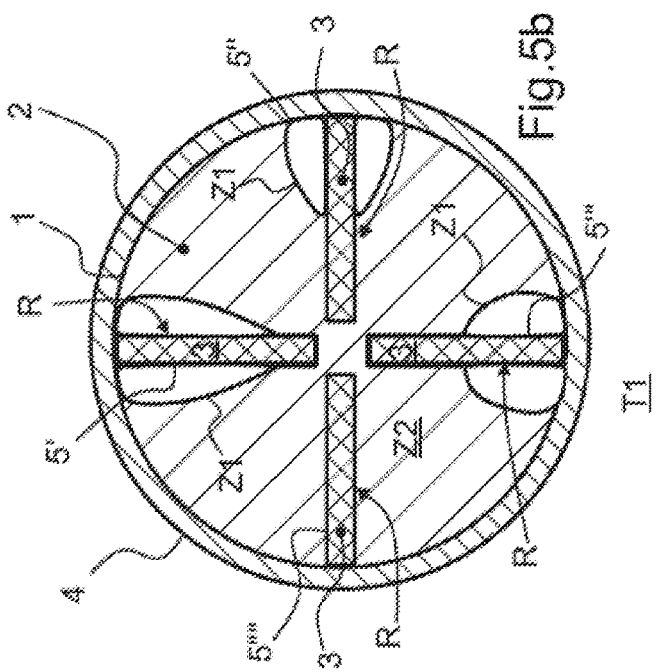
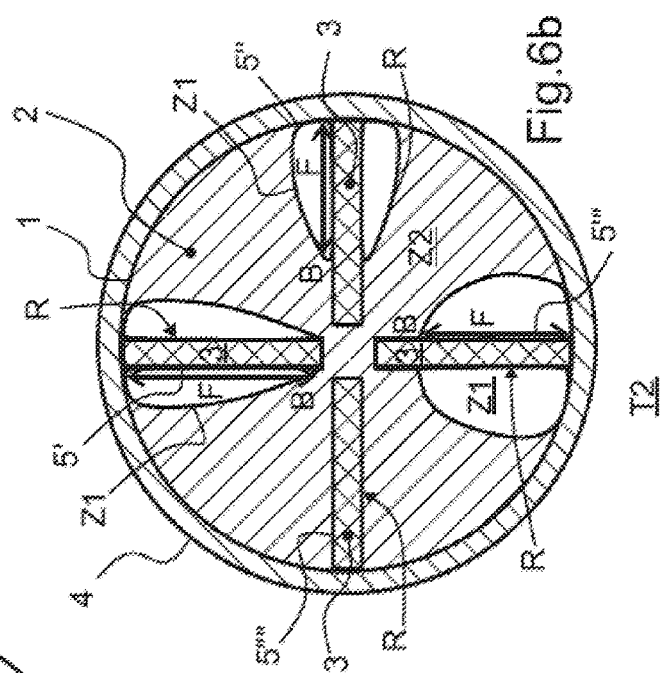
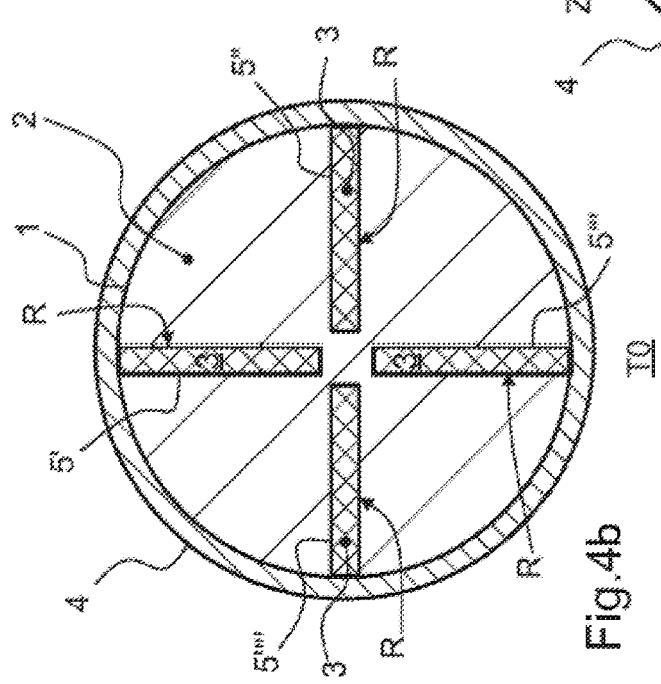

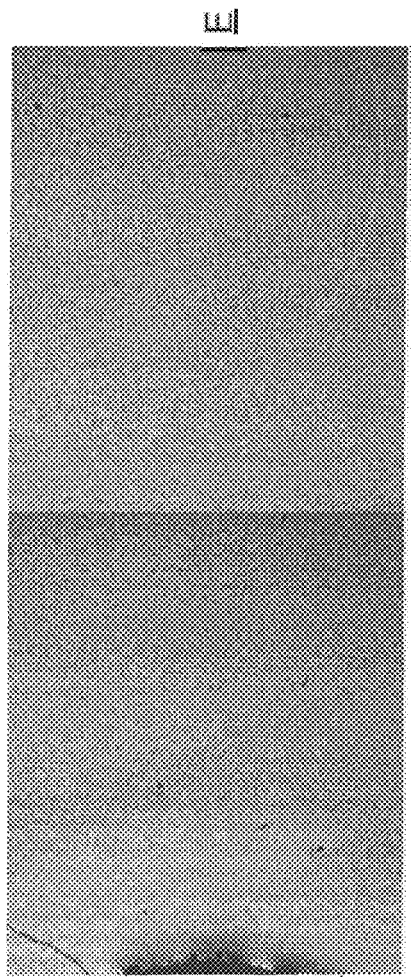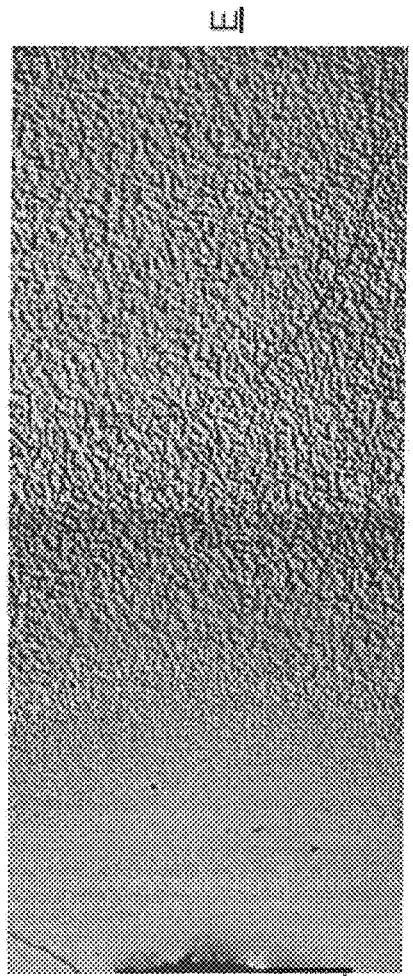

METHOD FOR DETECTING THE PRESENCE OR ABSENCE OF BIOLOGICAL PARTICLES

The invention relates to a method for detecting the presence or absence of at least one first inhibition zone comprised by a culture of biological particles on a culture medium in the presence of a chemical agent, said method of detection comprising a first step of seeding the culture medium with the biological particles, a second step in which the culture medium receives the chemical agent, and a third step of incubation of the culture medium.

Document WO 2011/125033 describes a method for detecting a cluster of biological particles on a surface. The biological particles are selected from microorganisms, such as bacteria, yeasts or fungi, or from plant or animal cells. The biological particles have a diameter or a principal dimension typically less than or equal to 100 µm. The surface is selected from an interface between a culture medium and a surrounding medium, such as air, a surface of a functionalized support or a surface of a microporous membrane.

The method comprises a plurality of steps, including a first step consisting of determining a topographical representation of the surface and a second step consisting of detecting, on the topographical representation, a contour delimiting a region that is likely to correspond to a cluster of biological particles, notably bacterial colonies, these steps being carried out using an electronic data processing means.

The first step is carried out on the basis of an optical method performed without contact and without sample preparation. According to a first variant, the first step is carried out by chromatic confocal microtopography. According to a second variant, the first step is carried out by strioscopy or by ombroscopy. More particularly, the first step comprises a phase in which the surface for which a three-dimensional representation is required is illuminated by a light source, a phase in which a signal corresponding to the light reflected or transmitted by this surface is detected by a light sensor, and a phase of determining a three-dimensional topographical representation of the surface from the detected signal.

The illumination of the surface may be directed from the surroundings toward the surface. When the illumination is not collimated, it can be focused on the zone to be measured. The light source may be spatially and/or temporally coherent, or it may be incoherent. It may be polychromatic or monochromatic. Detection may be performed by a one-dimensional image sensor, such as a linear array, or a two-dimensional image sensor such as a matrix, of the CMOS type, CCD, photomultiplier, photodiode, etc. This sensor may have a spectrometric function, allowing analysis of the spectrum of the detected light. It may also be coupled to a diaphragm, or pinhole, in order to constitute a device for confocal detection.

The bacterial colonies are observable by a setup using an ombroscopy technique. A parallel light beam passes through a Petri dish containing the culture medium, and then is focused onto a detector by a first lens. When a bacterial colony develops on the surface of the culture medium, it deflects the light rays, because of the variation in height, and therefore of the local slope formed on the surface. The radiation deflected by a variation in height, and/or a variation in index, on the observed surface is not captured by the detector. This device makes it possible to detect a local slope on a flat surface to be analyzed, resulting in the appearance of a dark zone on the image formed by the detector. Thus, according to this method, the bacterial colonies appear as dark spots on a light background, the latter corresponding to the surface of the culture medium. The representation of the surface topography of the medium is a two-dimensional representation, i.e. an image in which the change in intensity between two adjacent pixels reflects a variation in height of the illuminated surface.

In the field of diagnostics of the response of biological particles to a chemical agent, such as an antibiotic or the like, there is a need for a method for detecting the presence or absence of biological particles that is quick, effective and reliable. There are many imaging techniques for detecting the presence or absence of a zone of inhibition of the growth of biological particles in the presence of a chemical agent. However, the phenomena of diffusion of the chemical agent at the surface and within the agar of a culture medium, combined with the growth of the biological particles, notably microorganisms, on the surface of the medium, mean that it is difficult to detect an inhibition zone whose measured value is stable over time and is insensitive to the type of medium and chemical agent used. On the one hand, the concentration of chemical agent varies in the first hours of diffusion until a plateau value is reached; on the other hand, in the presence of a culture medium the biological particles develop, in a manner that is dependent on the concentration of chemical agent. The different types of chemical agent, notably antibiotics, may also have a different diffusion behavior, and they have their own refractive index. Determination of a stable boundary between the growth zone, where the particles grow, and the inhibition zone, where the concentration of the chemical agent is too high for the particles to grow, is thus particularly complex. To overcome this drawback, the recommendations of the regulatory agencies such as the NCCLS (National Committee for Clinical Laboratory Standards) or EUCAST (European Committee on Antimicrobial Susceptibility Testing) are to undertake a single reading at eighteen hours, or at twenty hours, optionally at twenty-four hours in order to be sure that the phenomena of diffusion of the chemical agent have stabilized in and on the agar and that the measured value of the inhibition zone is reliable and repeatable, compared to the values of reference measurements. More particularly, it is therefore desirable to have such a method with an improved diagnosis time, notably less than eight hours, with optimized reliability and repeatability.

One aim of the present invention is therefore to propose a method for detecting the presence or absence of a first inhibition zone that is reliable, and whose repeatability is optimized, regardless of the culture medium used and the type of chemical agent. Furthermore, another aim of the invention is to propose a method for measuring a first inhibition zone that is quick and is stable over time, notably throughout the diffusion of the chemical agent in the culture medium. Another aim of the invention is to propose a method for detecting the presence or absence of biological particles that is reliable, whose repeatability is optimized and that offers a response time to the presence of a chemical agent that is short, notably equal to eight hours, and more particularly that is quicker than a method known from the prior art that is based on naked-eye observation of the biological particles. Another aim of the present invention is to propose a detecting device for carrying out said method of detection.

One method of the present invention is a method for detecting the presence or absence of at least one first inhibition zone comprised by a culture of biological particles on a culture medium in the presence of a chemical agent.

The method of detection comprises a first step of seeding the culture medium with the biological particles, a second step in which the culture medium receives a support impregnated with the chemical agent, and a third step of incubation of the culture medium.

According to the present invention, the method of detection comprises a fourth step of measuring the first inhibition zone of the culture medium that comprises a first phase of taking an image of the first inhibition zone by ombroscopy.

According to a first embodiment of the present invention, the fourth step of measurement comprises measuring a distance between the impregnated support and an edge of the first inhibition zone.

According to a second embodiment of the present invention, the fourth step of measurement comprises measuring a diameter of the first inhibition zone. In this embodiment, this fourth step may advantageously be followed by at least one operation of estimating a minimum inhibitory concentration, for determining the sensitivity of the biological particles to the chemical agent.

The method of detection advantageously comprises a fifth processing step, which comprises a second phase of taking a control photograph of the culture medium.

The control photograph is for example a photograph of a ruler arranged on the culture medium.

The method of detection advantageously comprises a third phase of superimposing the image and the control photograph to form a normed representation.

The fifth processing step advantageously comprises a fourth phase of locating a reference of the ruler.

The fifth processing step advantageously comprises a fifth phase of processing the normed representation.

The fifth phase advantageously comprises at least one smoothing operation for homogenizing the normed representation.

The fifth phase advantageously comprises at least one operation of stretching the dynamics of the pixel intensity of the normed representation to form a contrast histogram of the normed representation.

The fifth phase advantageously comprises at least one thresholding operation of the normed representation, which comprises detection of a threshold and determination of a contour of the normed representation.

The method of detection advantageously comprises at least one operation of estimating a minimum inhibitory concentration, for determining the sensitivity of the biological particles to the chemical agent.

The first phase of taking the image and the second phase of taking the control photograph are for example phases that are performed continuously.

The first phase of taking the image and the second phase of taking the control photograph are for example phases that are performed with a defined time lapse.

Calculating means of the present invention are calculating means configured for carrying out said method of detection, preferably for carrying out the measuring step 104 and/or the processing step 105.

A processor of the present invention advantageously comprises said calculating means.

A detecting device of the present invention is mainly recognizable in that the detecting device comprises a processor of this kind.

The detecting device advantageously comprises a sensing means, a light source able to produce collimated light rays and an optical focus.

The sensing means advantageously comprises a sensing axis, which is arranged orthogonally relative to a first plane over which the culture medium extends.

The light source is advantageously positioned on the sensing axis, the culture medium being interposed between the sensing means and the light source.

The detecting device advantageously comprises at least one semireflecting mirror for returning the light rays emitted by the light source to the culture medium.

Other features and advantages of the present invention will become clear on reading the description that will be given of embodiment examples, referring to the figures in the appended drawings, in which:

FIGS. 4, 5 and 6 are schematic top views of the Petri dish illustrated in FIG. 1 at three separate respective times according to a first embodiment of the present invention.

FIGS. 4b, 5b and 6b are schematic top views of the Petri dish illustrated in FIG. 1 at three separate respective times according to a third embodiment of the present invention.

FIGS. 13a and 13b are images taken by the detecting device illustrated in FIG. 10, of a culture of *Escherichia coli* (ATCC 25922) in the presence of ampicillin, at a measurement time $T_1$ of two hours and four hours, respectively.

FIGS. 16a, 16b, 16c, 16d, 16e and 16f are images taken by the detecting device illustrated in FIG. 9, of a culture of

*Escherichia coli* (ATCC 35218) in the presence of piperacillin-tazobactam at a measurement time $T_1$ of zero hour, two hours, four hours, six hours, eight hours and twenty-four hours, respectively.

Figure 17:
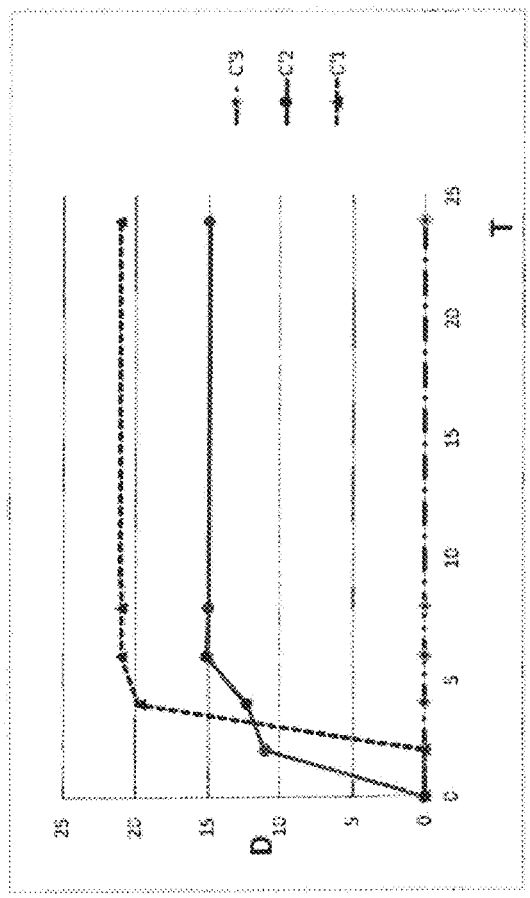

FIG. 17 is a schematic illustration of the time-dependent evolution of the diameter of the inhibition zone of *Escherichia coli* (ATCC 25922), of *Staphylococcus aureus* (ATCC 25923) and of *Escherichia coli* (ATCC 35218) in the presence of ampicillin observed by carrying out the method of detection of the present invention.

Figure 18:
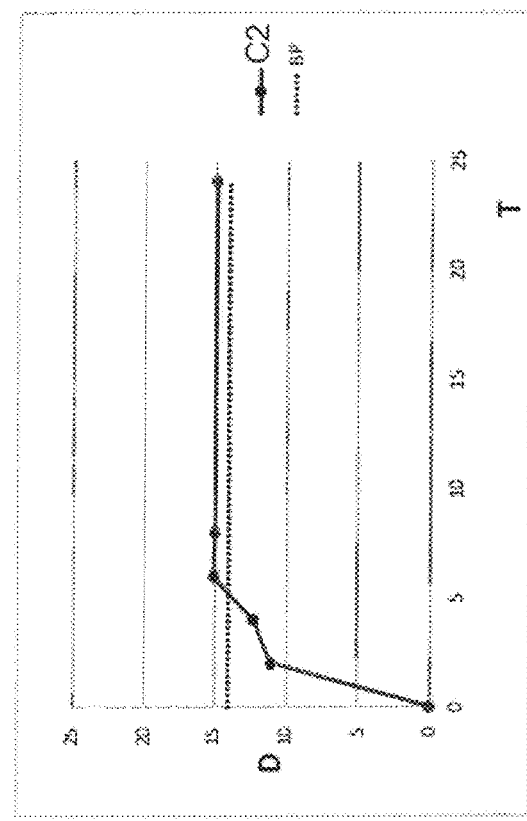

FIG. 18 is a schematic illustration of the time-dependent evolution of the diameter of the inhibition zone of *Escherichia coli* (ATCC 35218) in the presence of ampicillin-sulbactam observed by carrying out the method of detection of the present invention.

Figure 2:
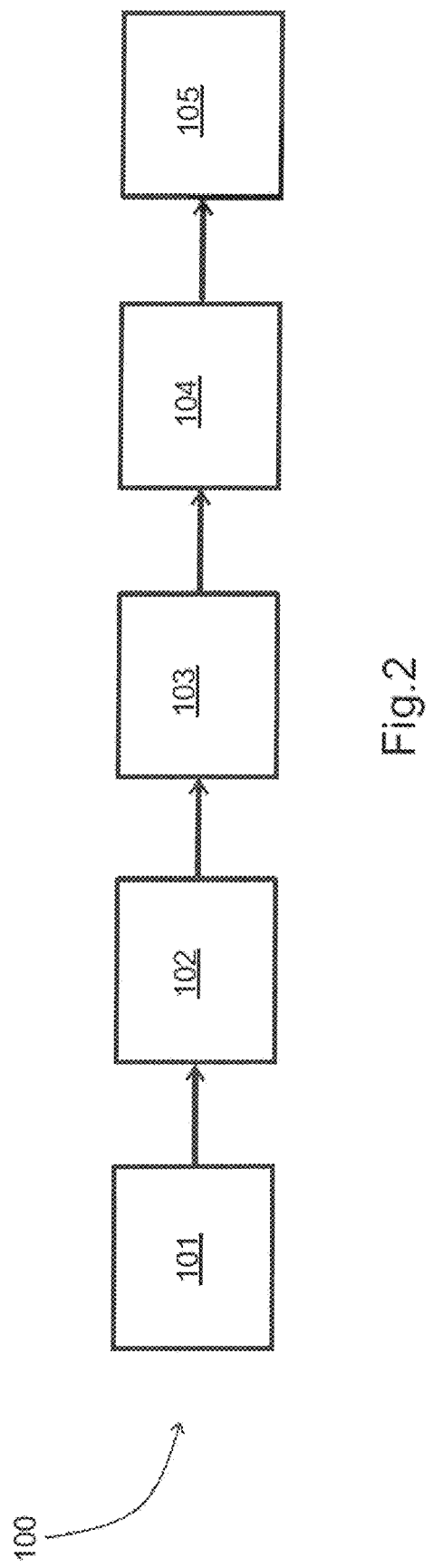
FIG. 2 is a schematic view of the method of detection of the present invention.
Figure 19:
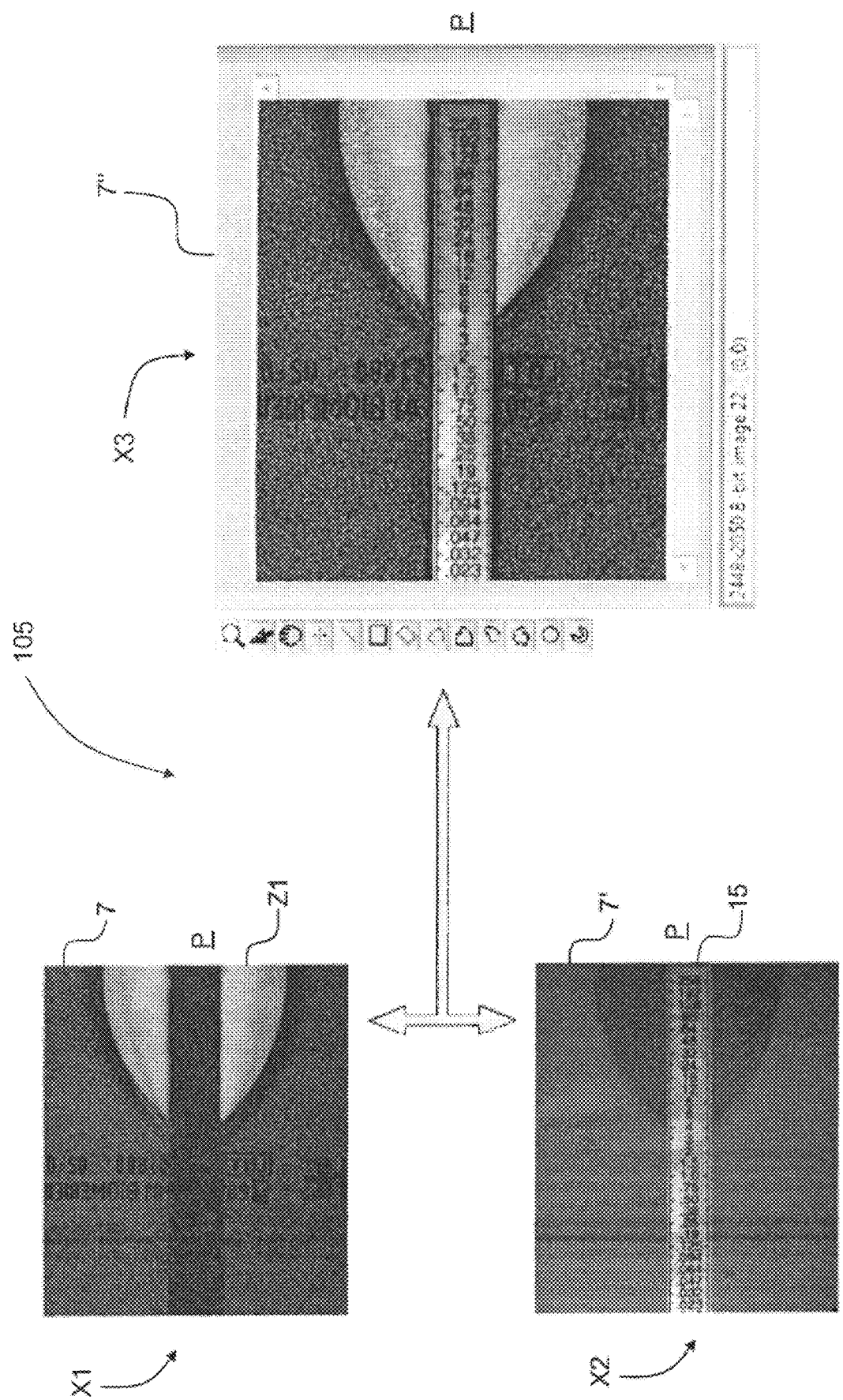
Figure 20:
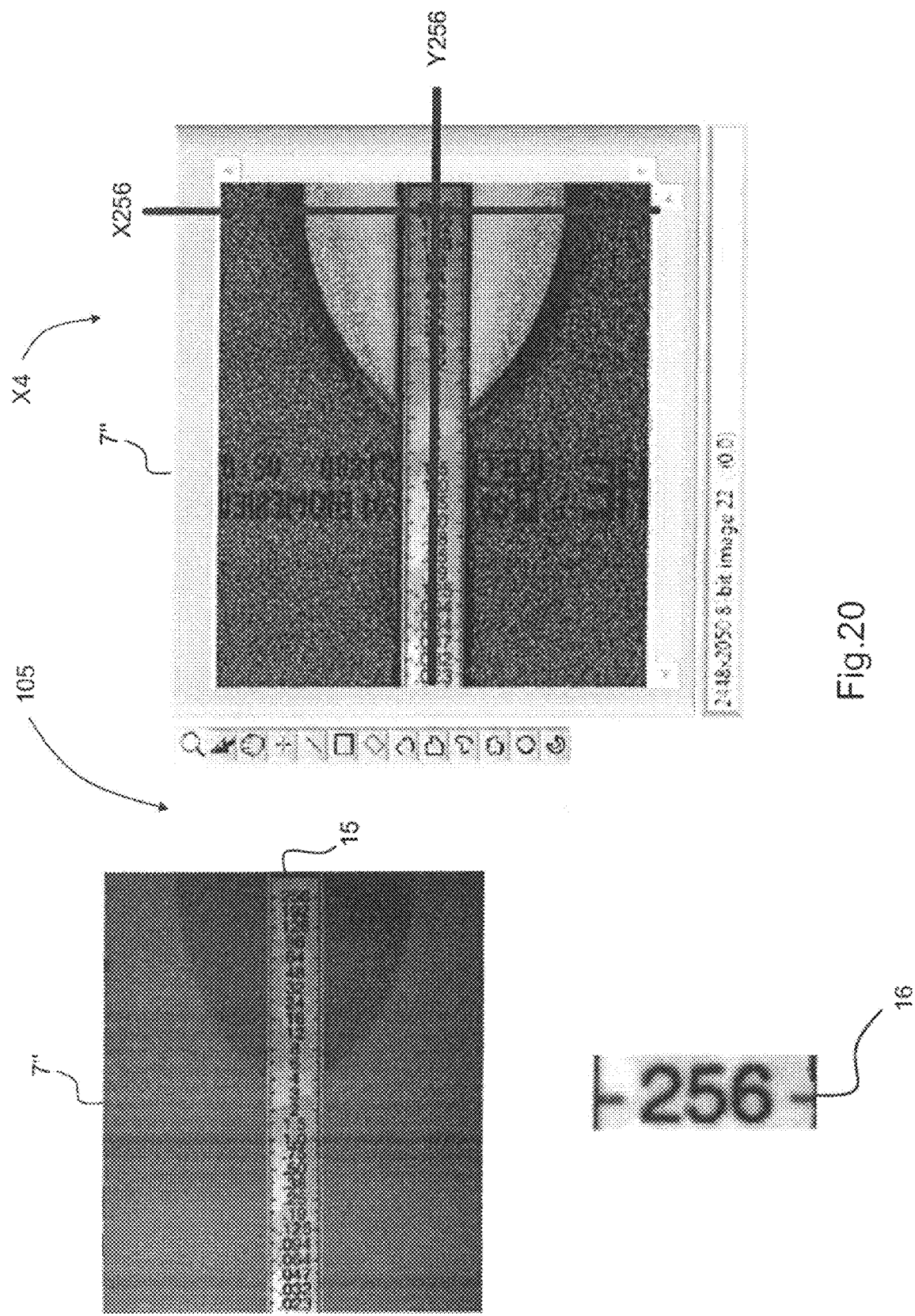

FIGS. 19 and 20 are schematic views of respective steps of the method of detection illustrated in FIG. 2.

FIGS. 21 to 25 are schematic illustrations of successive operations of a fifth phase of the method of detection illustrated in FIG. 2.

FIGS. 26 to 30 are schematic illustrations of normed representations obtained by carrying out the method of detection illustrated in FIG. 2.

Figure 9:
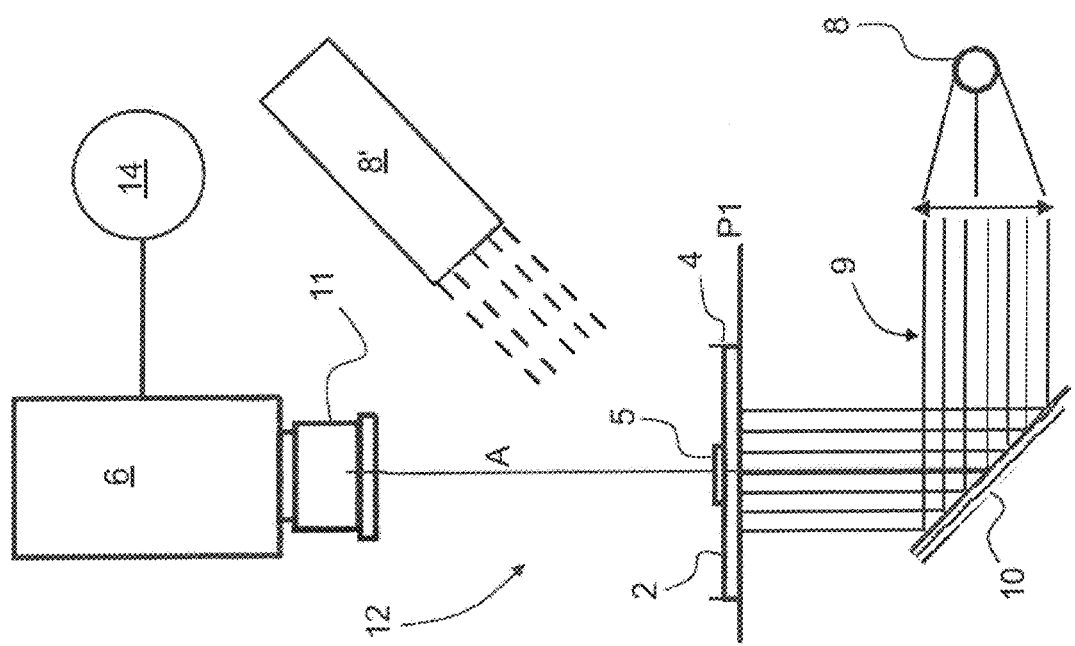
FIG. 9 is a schematic illustration of a second embodiment of the first variant of the detecting device for carrying out the method of detection illustrated in FIG. 2.
Figure 31C:
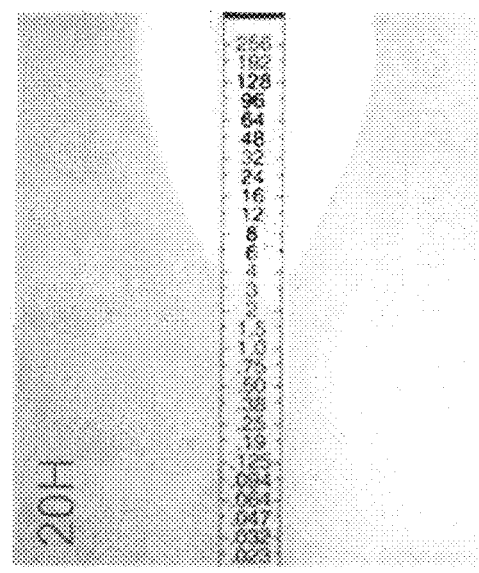
Figure 31B:
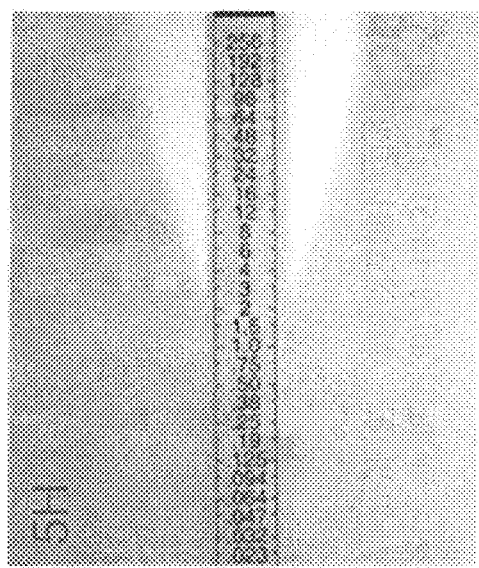
Figure 31A:
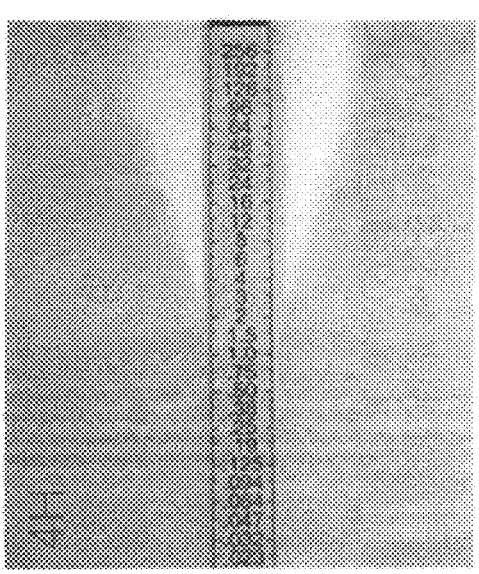

FIGS. 31a, 31b, 31c are images taken by the detecting device illustrated in FIG. 9, of a suspension of *Staphylococcus aureus* on a chromogenic culture medium ChromoID™ MRSA Smart opaque (bioMérieux, Ref. 413050), in the presence of cefoxitin at a respective measurement time $T_1$ of four hours, five hours and twenty hours.

Figure 32C:
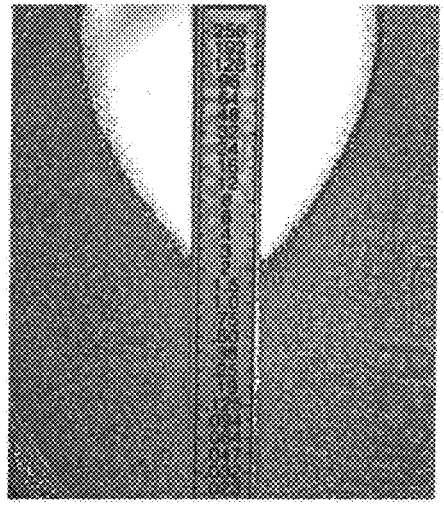
Figure 32B:
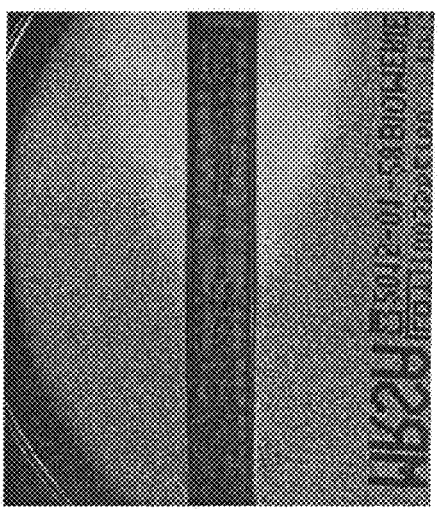
Figure 32A:
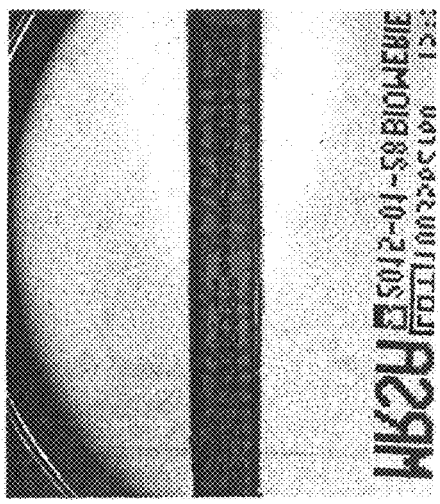

FIGS. 32a, 32b, 32c are images taken by the detecting device illustrated in FIG. 9, of a suspension of *Staphylococcus aureus* on a chromogenic culture medium ChromoID™ MRSA transparent (bioMérieux, Ref. 43451), in the presence of cefoxitin at a respective measurement time $T_1$ of four hours, five hours and twenty hours.

Figure 33A:
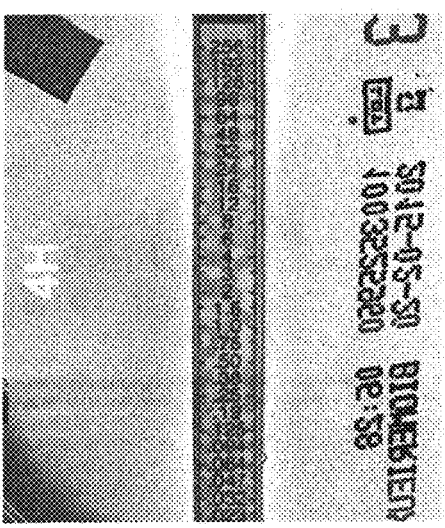
Figure 33B:
Figure 33C:
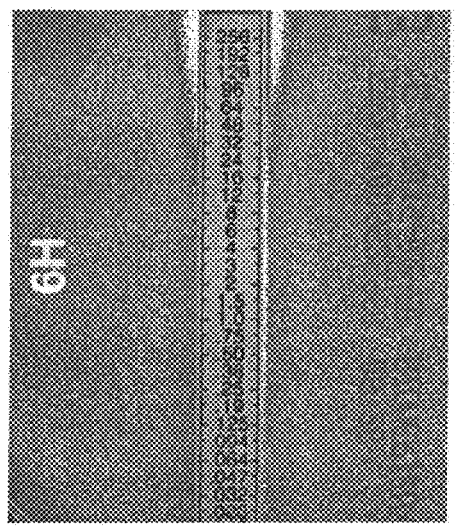

FIGS. 33a, 33b, 33c are images taken by the detecting device illustrated in FIG. 9, of a suspension of *Staphylococcus epidermidis* on a chromogenic culture medium CPS® ID 3 (CPS3) (bioMérieux, Ref. 43541), in the presence of gentamicin at a respective measurement time $T_1$ of four hours, five hours, six hours.

Figure 34A:
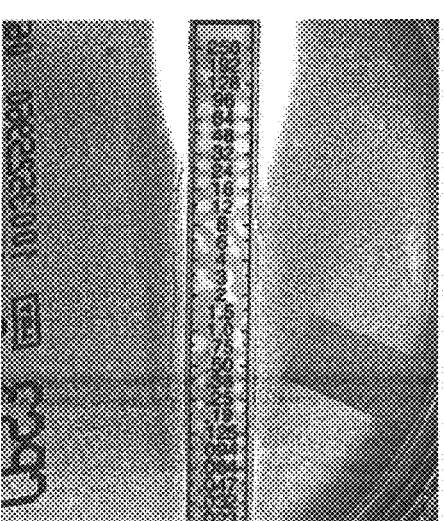
Figure 34B:
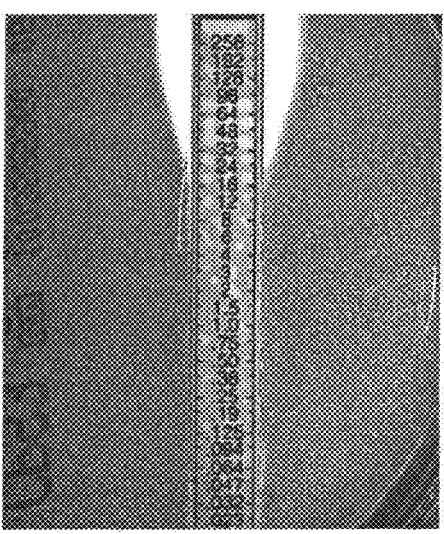
Figure 34C:
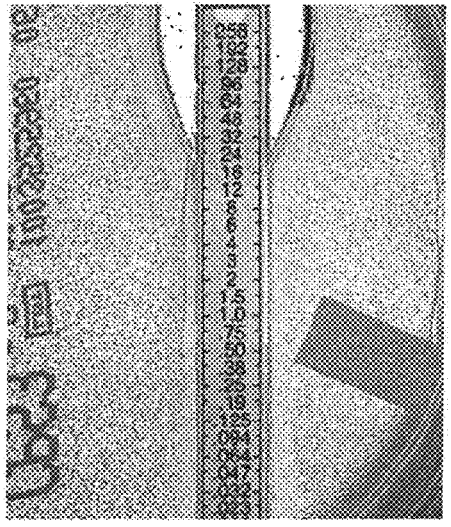

FIGS. 34a, 34b, 34c are images taken by the detecting device illustrated in FIG. 9, of a suspension of *Staphylococcus aureus* on a chromogenic culture medium CPS® ID 3 (CPS3) (bioMérieux, Ref. 43541), in the presence of gentamicin at a respective measurement time $T_1$ of four hours, five hours, six hours.

Figures 35A, 35B, 35C:
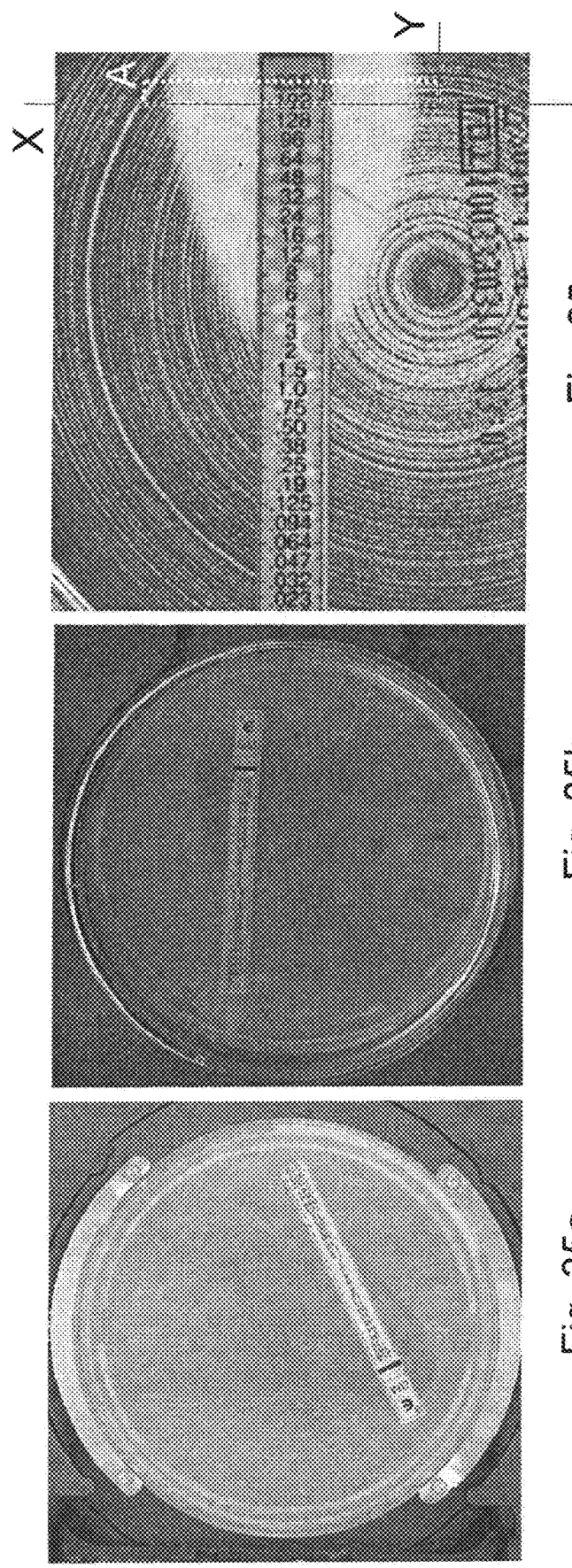

FIGS. 35a, 35b, 35c are images taken by different detecting devices, respectively "SIU", "ADVENCIS" and the device illustrated in FIG. 9, of a culture of *Escherichia coli* on a Mueller Hinton E culture medium (bioMerieux MHE, Ref. 413822), in the presence of gentamicin at a measurement time $T_1$ of six hours.

Figure 36:
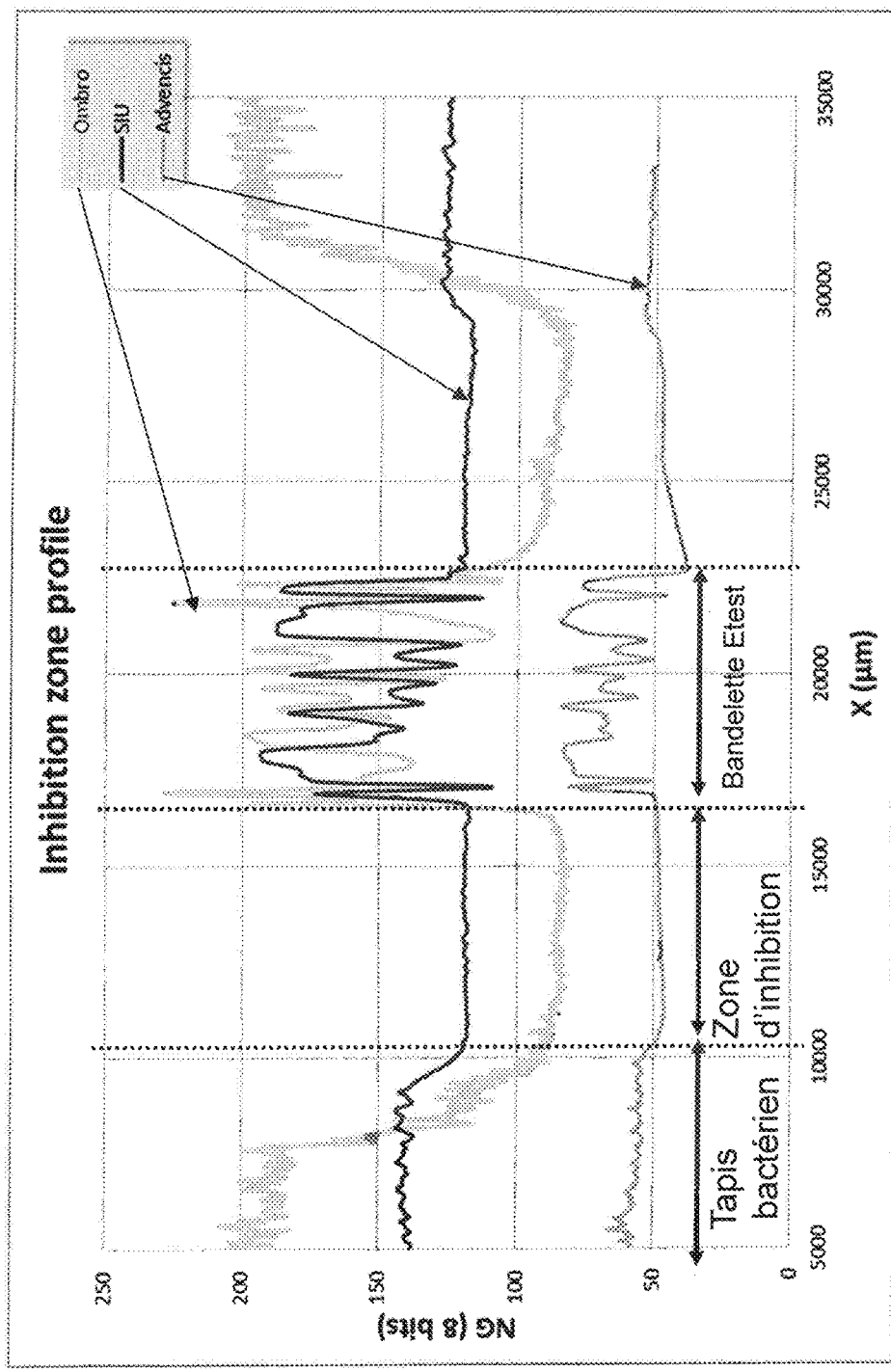

FIG. 36 is a schematic illustration of three gray level profiles observed on the images in FIGS. 35a, 35b and 35c, taken by three detecting devices.

Figure 37A:
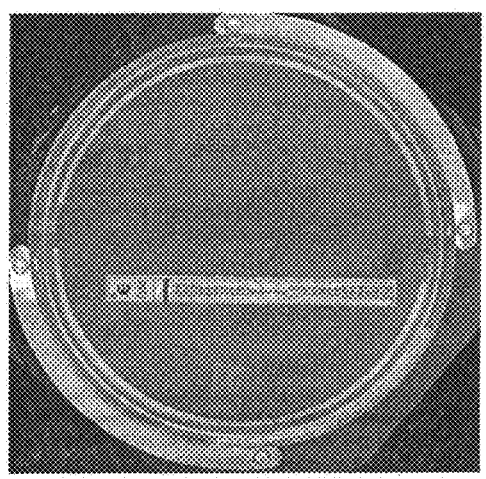
Figure 37B:
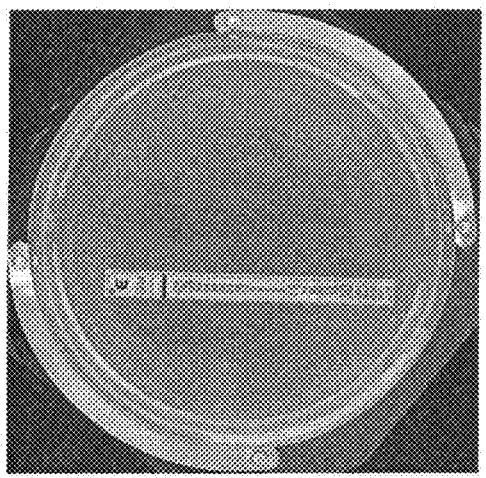
Figure 37C:
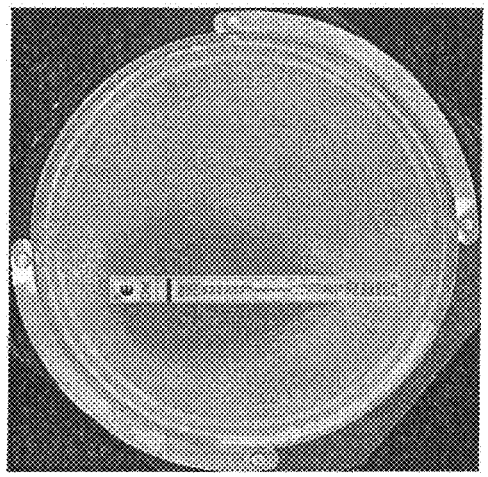

FIGS. 37a, 37b, 37c are images taken by a detecting device, "SIU", of a suspension of *Escherichia coli* (ATCC "American Type Culture Collection" 25922) on a Mueller Hinton E culture medium (bioMerieux MHE, Ref. 413822), in the presence of gentamicin after incubation at a measurement time $T_1$ of four hours, six hours and twenty-four hours, respectively.

Figure 38A:
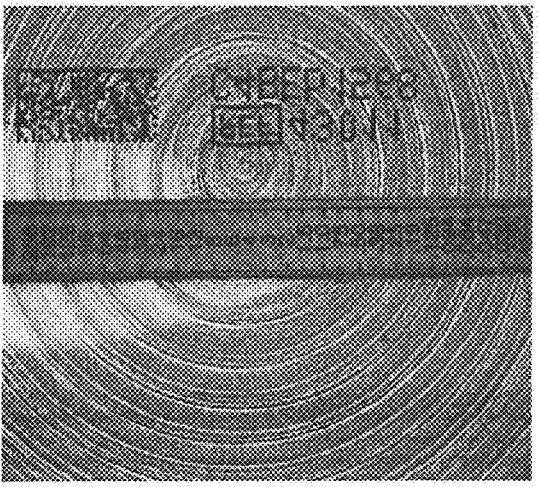
Figure 38B:
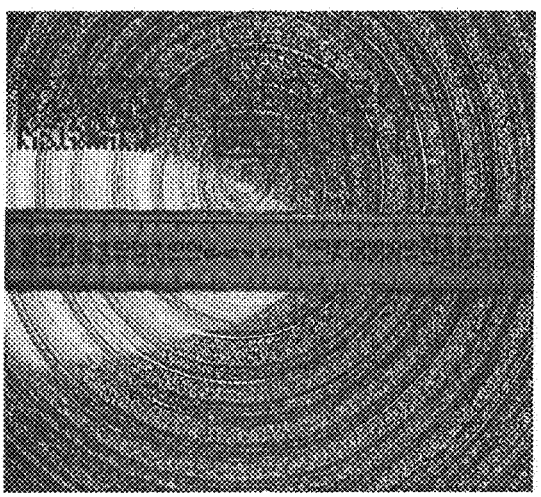
Figure 38C:
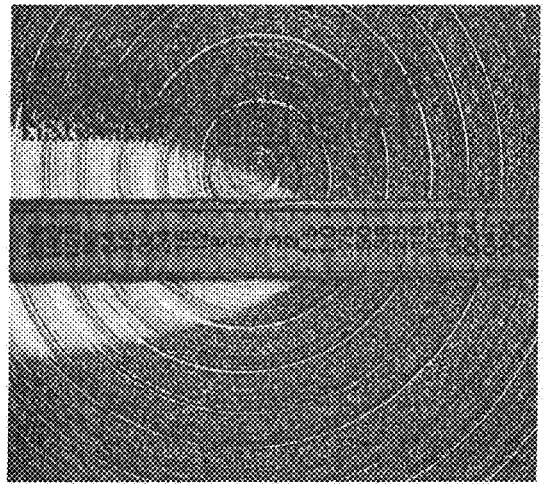

FIGS. 38a, 38b, 38c are images taken by a detecting device, by ombroscopy according to FIG. 9, of a suspension of *Escherichia coli* (ATCC 25922) on a Mueller Hinton E culture medium (bioMérieux MHE, Ref. 413822), in the presence of gentamicin after incubation at a measurement time $T_1$ of three hours thirty minutes, six hours and twenty-four hours, respectively.

Figures 39A, 39B:
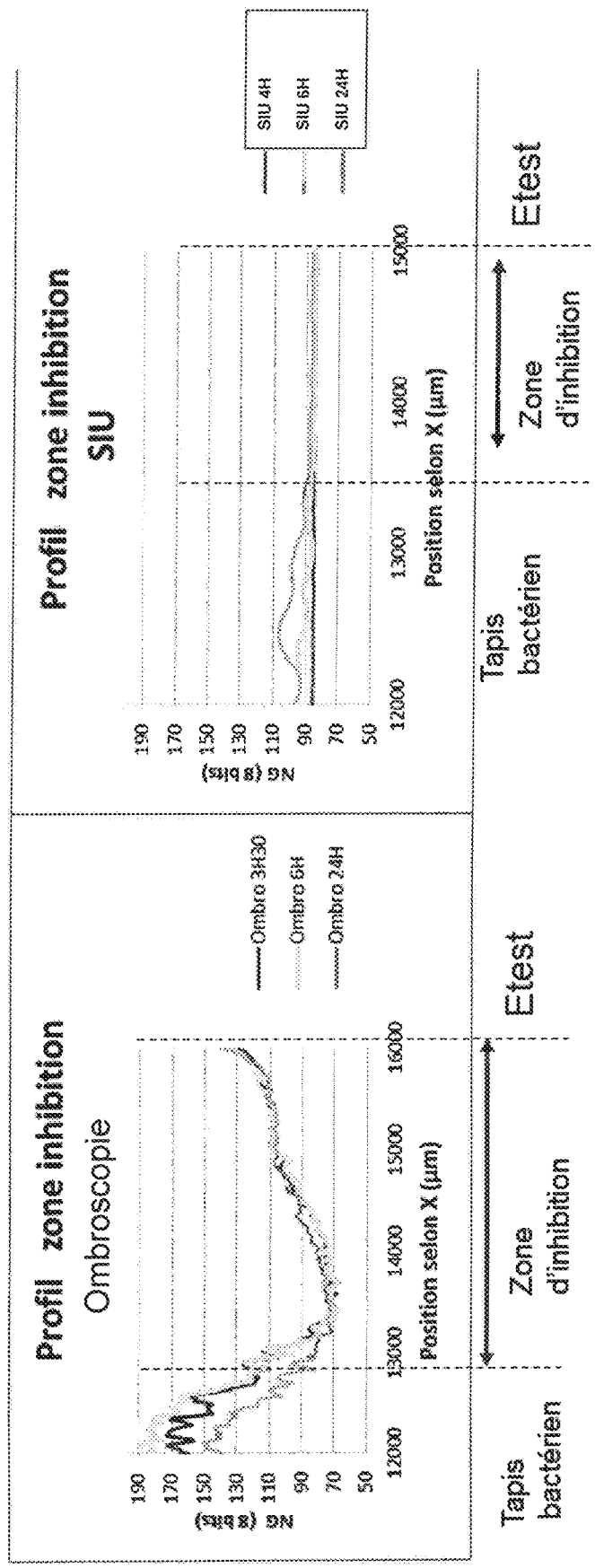

FIGS. 39a and 39b are schematic illustrations of three gray level profiles observed at each measurement time from two devices used for obtaining FIGS. 37a, 37b and 37c and 38a, 38b, 38c.

Figure 1:
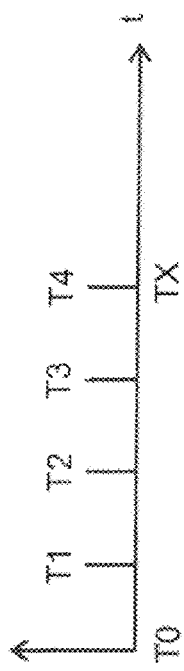
FIG. 1 is a sectional view of a Petri dish used for carrying out a method of detection of the present invention.

Referring to FIG. 1 or 2, in the medical and/or pharmaceutical field, it is often necessary to use a method of detection 100 of the presence or absence of biological particles 1 on a culture medium 2 in contact with a chemical agent 3. The culture medium 2 receives, in succession, the biological particles 1, and then the chemical agent 3 that is able to inhibit the development of certain biological particles 1. The biological particles 1 are selected indifferently from microorganisms, such as bacteria, yeasts or fungi, or from plant or animal cells. The culture medium 2 is preferably agar, a layer of agar or the like. The chemical agent 3 is notably an antibiotic, an antifungal, an antimycobacterial or a similar compound.

More particularly, it is desirable to be able to characterize, reliably and quickly, a response of the biological particles 1 to the presence of the chemical agent 3, said response commonly being classified according to one of the following three statements: sensitive, intermediate or resistant. "Sensitive" means that growth, or even survival, of the biological particles 1 in the presence of the chemical agent 3 is impossible, starting from a certain concentration of chemical agent 3. "Intermediate" means that growth of the biological particles 1 in the presence of the chemical agent 3 is compromised, starting from a certain concentration of chemical agent 3. "Resistant" means that growth of the biological particles 1 in the presence of the chemical agent 3 is possible.

Figure 3:
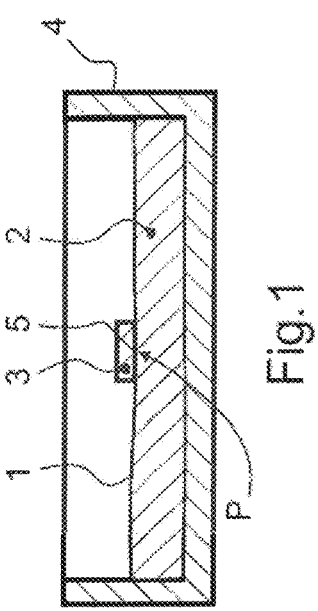
FIG. 3 is a schematic illustration of sequences of the method of detection of the present invention.

A method of detection 100 of this kind notably finds frequent application in the field of medical and/or pharmaceutical diagnostics employed for detecting a pathology in a patient. As a result, said method of detection 100 is desired to be reliable in the sense that the nature of the aforementioned response of the biological particles 1 to the chemical agent 3 is desired, certain, without doubt and unambiguous. It also follows that such a method of detection 100, whose successive sequences are illustrated in FIG. 3, is desired to be quick, with a response time, which elapses between an initial time $T_0$ at which the biological particles 1 are brought into contact with the chemical agent 3 and a detection time $T_X$ at which said reliable response is obtained, which is desired to be as short as possible, and is notably less than eight hours. It also follows that it is desirable that such a method of detection 100 should comprise an appropriate repeatability. Such aims are attained advantageously by carrying out the method of detection 100 of the present invention.

In general terms, referring to FIG. 2, the method of detection 100 of the present invention comprises a first step 101 of seeding the culture medium 2 with an extract of biological particles 1. The extract of biological particles 1 is for example a raw sample of biological particles 1 taken from the patient directly. In this case the raw sample undergoes a preculture phase for isolating strains of biological particles 1 present, in the case of a sample comprising a diversity of biological particles 1, and increase of the biological particles 1 selected and isolated. The extract of biological particles 1 is for example a sample prepared, notably filtered, centrifuged and/or purified in a similar manner. The sample of biological particles 1 has a biomass of biological particles 1 that is sufficient to be analyzed validly, such as a standard at a concentration of 0.5 McFarland. The extract of biological particles 1 is for example from urine, blood, cerebrospinal fluid or a similar biological fluid.

The culture medium 2 is for example flooded with the extract of biological particles 1, or the culture medium 2 is seeded with biological particles 1 by swabbing, or the culture medium 2 receives the biological particles by spreading them using a rake. Then, the Petri dish 4 is agitated transversely to distribute the extract of biological particles 1 as uniformly as possible on the culture medium 2, and then any supernatant is removed from the Petri dish 4. The first step of seeding 101 may have features different from those described above without departing from the rules of the present invention.

The method of detection 100 then comprises a second step 102 of receiving at least one dose of the chemical agent 3 at the initial time point $T_0$, for example starting from placement of at least one impregnated support 5 inoculated with the chemical agent 3 on a receiving zone R of the impregnated support 5 on the culture medium 2.

The impregnated support 5 is for example a disk impregnated with the chemical agent 3, the disk having the overall conformation of a thin slice of a cylinder. The disk comprises an amount of chemical agent 3 that is homogeneous overall in its volume.

The impregnated support 5 is for example also a slender strip, of overall rectangular conformation. The strip comprises for example a concentration of chemical agent 3 that follows an increasing concentration gradient from one short edge to an opposite short edge of the strip.

The impregnated support 5 is for example also reduced to a droplet of water containing the chemical agent 3.

According to one embodiment illustrated in FIGS. 4, 5 and 6, the culture medium 2 receives a single impregnated support 5. The receiving zone R is preferably formed by a central point of the Petri dish 4.

Figure 5A:
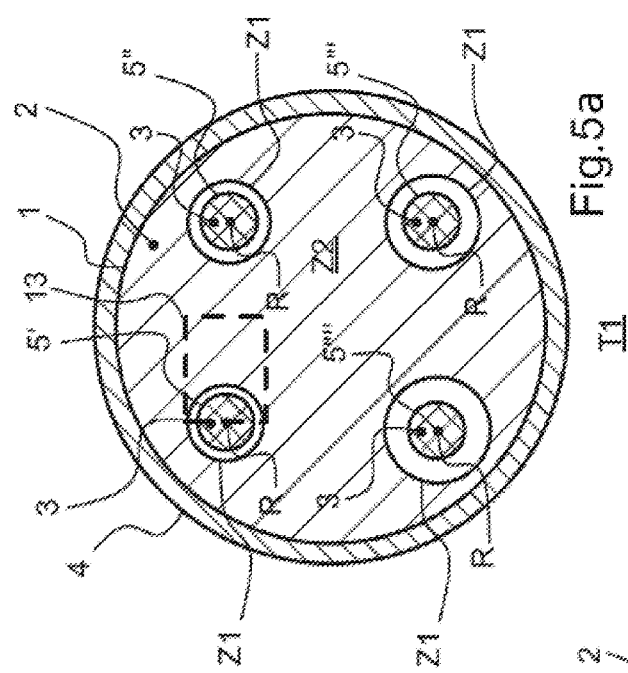
FIGS. 4a, 5a and 6a are schematic top views of the Petri dish illustrated in FIG. 1 at three separate respective times according to a second embodiment of the present invention.
Figure 6A:
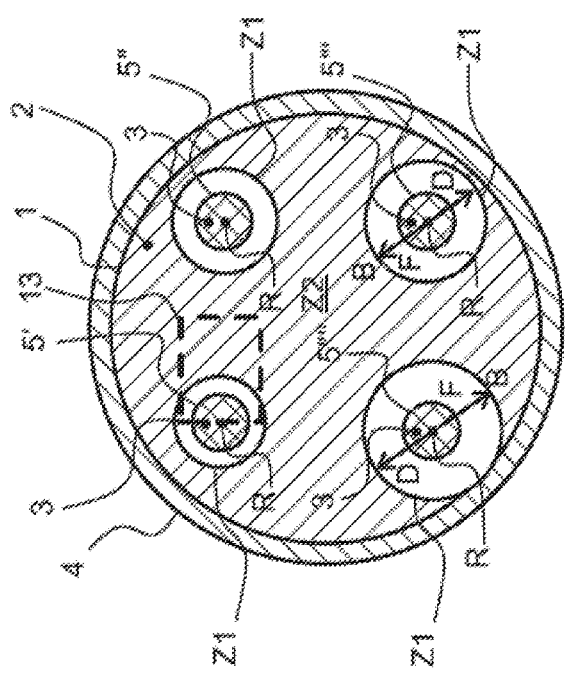
Figure 4A:
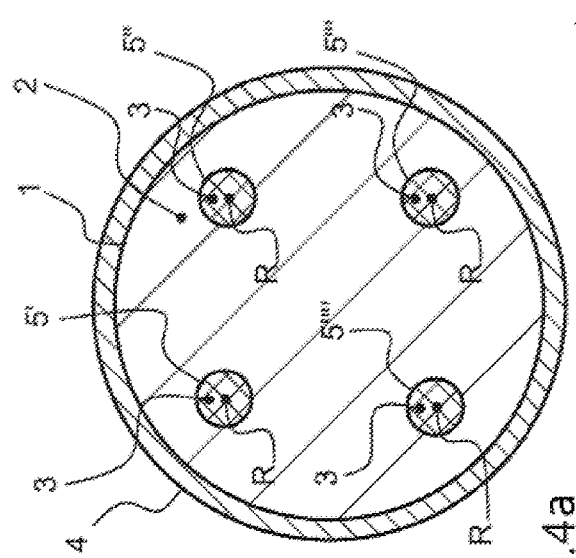
Figure 8:
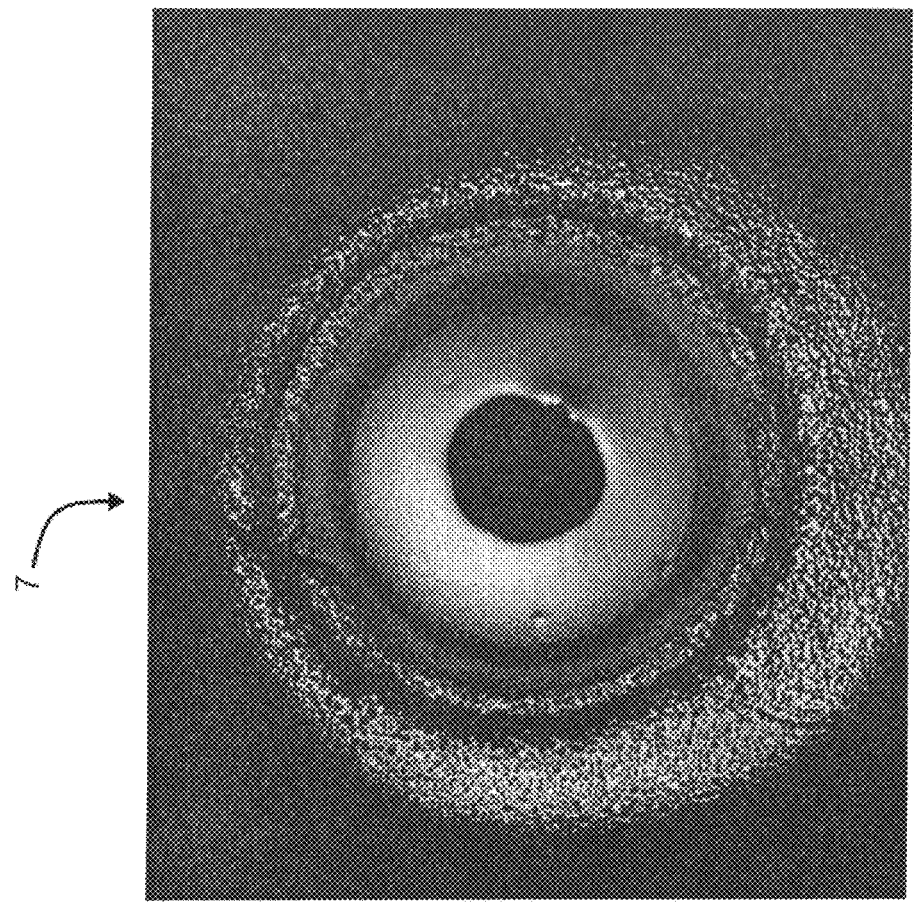
FIG. 8 is an illustration of an image obtained from the detecting device illustrated in FIG. 7.

According to another embodiment illustrated in FIGS. 4a, 5a and 6a, the culture medium 2 receives a plurality of impregnated supports 5',5",5"',5"", each impregnated support 5',5",5"',5"" comprising for example its own concentration of chemical agent 3 different from that of the other impregnated supports 5',5",5"',5"". For example, a first impregnated support 5' comprises a first concentration of chemical agent 3 that is lower than a second concentration of chemical agent 3 comprised by a second impregnated support 5", the second concentration being lower than a third concentration of chemical agent 3 comprised by a third impregnated support 5"', the third concentration being lower than a fourth concentration of chemical agent 3 comprised by a fourth impregnated support 5"'. There is a plurality of receiving zones R, which are for example formed by points that are equidistant from the culture medium 2. According to another embodiment, each impregnated support 5',5",5"',5"" comprises a chemical agent 3 different from that of the other impregnated supports 5',5",5"',5"".

According to yet another embodiment illustrated in FIGS. 4b, 5b and 6b, the culture medium 2 receives a plurality of impregnated supports 5',5",5"',5"", which are each conformed as a strip and are impregnated with a respective chemical agent 3. There is a plurality of receiving zones R and they are for example conformed according to respective radii of the Petri dish 4.

These variants aim, depending on the circumstances, to optimize the efficiency and speed of analysis of the response of the biological particles 1 to various chemicals 3 and to different concentrations of the latter, with an optimized rate of analysis. According to these different variants, the second receiving step 102 results in instantaneous delivery of the chemical agent 3 to the interior of the culture medium 2, which is propagated to the interior of the culture medium 2 from the impregnated support 5,5',5",5"',5"".

The method of detection 100 then comprises a third step of incubation 103, during which the biological particles 1 interact with the chemical agent 3 during a defined time lapse corresponding to an incubation time. Preferably, said incubation step 103 is carried out at a constant temperature, for example of 37° C., in a controlled environment. The incubation time is preferably of the order of some hours, and notably of two hours, or four hours, or six hours, or eight hours, or eighteen hours, or twenty hours, or even twenty-four hours. Typically, the incubation time is equivalent to the observation times $T_1, T_2$ described below.

Referring respectively to FIGS. 5, 5a, 5b on the one hand and FIGS. 6, 6a, 6b on the other hand, as a result of these arrangements, during observation at a first observation time $T_1$, and then at a second observation time $T_2$, there is formation of at least one first inhibition zone $Z_1$ of the biological particles 1, within which the biological particles 1 are inhibited, in the favorable case when the latter are sensitive to the chemical agent 3. In this case, either the biological particles 1 are destroyed, or their growth is stopped. Otherwise, the culture medium 2 remains homogeneous with a concentration of biological particles 1 that is homogeneous overall within all of the culture medium 2. In this case, we observe absence of an inhibition zone $Z_1$, in other words we observe growth of biological particles 1 in the presence of the chemical agent 3.

In FIGS. 5,5a and FIGS. 6.6a, the inhibition zones $Z_1$ are circular overall and are centered on the receiving zone R. Each inhibition zone $Z_1$ of the biological particles 1 tends to increase radially from the receiving zone R, between the first observation time $T_1$ illustrated in FIGS. 5, 5a, and the second observation time $T_2$ illustrated in FIGS. 6, 6a.

In FIG. 5b and FIG. 6b, the inhibition zones $Z_1$ are ellipsoidal overall and are distributed symmetrically on either side of the receiving zone R. Each inhibition zone $Z_1$ of the biological particles 1 tends to increase centrifugally from the receiving zone R, between the first observation time $T_1$ illustrated in FIG. 5b and the second observation time $T_2$ illustrated in FIG. 6b.

The method of detection 100 then comprises a fourth step of measurement 104 of the first inhibition zone $Z_1$ by ombroscopy. The fourth measurement step 104 comprises a phase of measuring a distance F that extends between the receiving zone R and an end edge B of the inhibition zone $Z_1$.

In FIGS. 6 and 6a, the distance F is equivalent to the diameter D of the inhibition zone $Z_1$.

In FIG. 6b, the distance F is equivalent to a length of the inhibition zone Z1 taken along the impregnated support 5.

Figure 7:
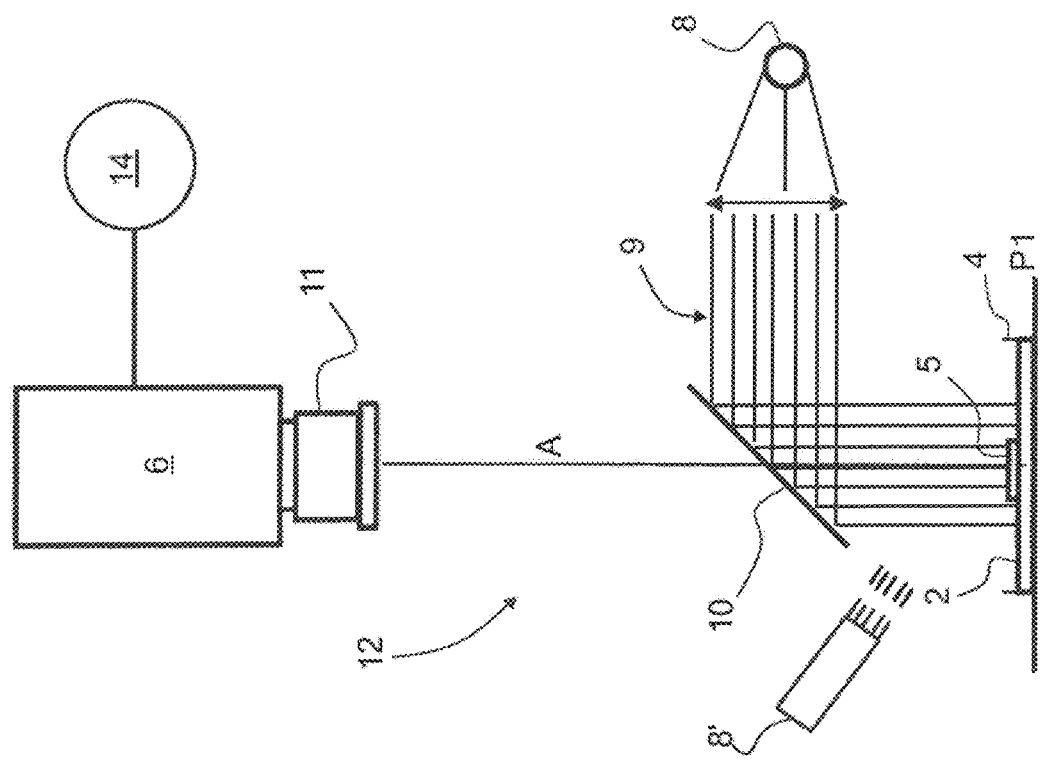
FIG. 7 is a schematic illustration of a first embodiment of a first variant of a detecting device for carrying out the method of detection illustrated in FIG. 2.
Figure 10:
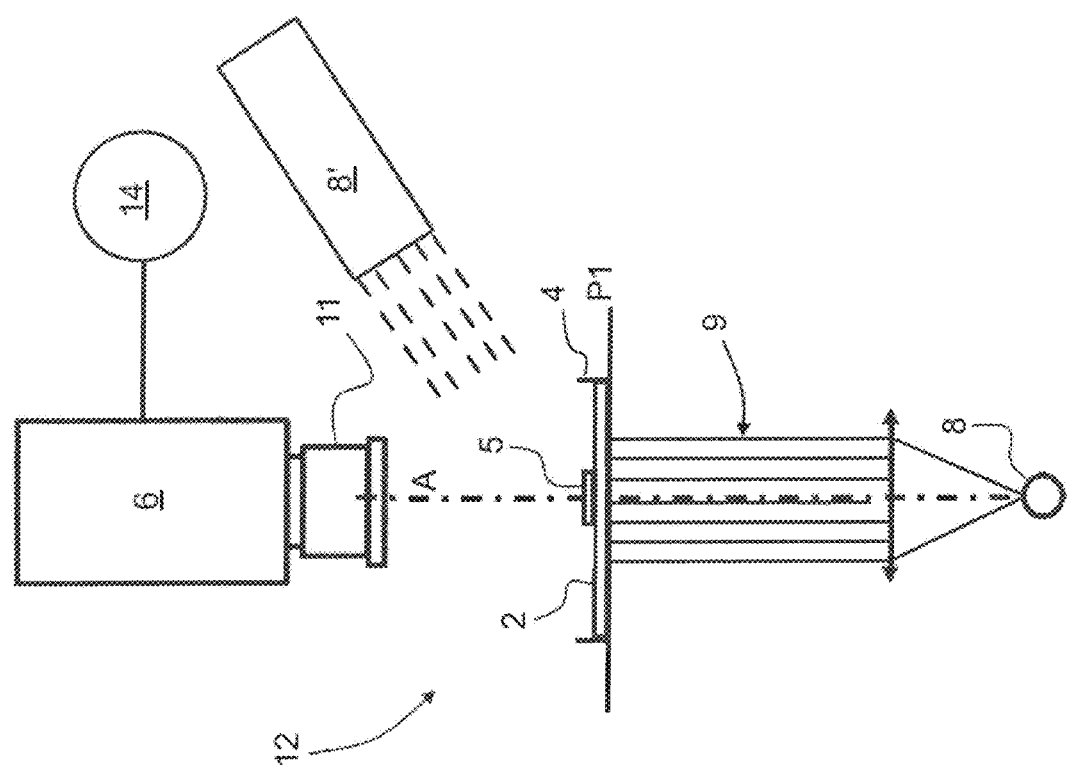
FIG. 10 is a schematic illustration of a second variant of the detecting device for carrying out the method of detection illustrated in FIG. 2.

Referring to FIGS. 7, 9 and 10, the fourth measurement step 104 employs a sensing means 6 of the image 7 and a light source 8. In general terms, the light source 8 illuminates the Petri dish 4, whose image 7 is taken either at a regular time interval by the sensing means 6, or after a defined time lapse for each Petri dish 4, or continuously on one and the same Petri dish 4. The sensing means 6 comprises a sensing axis A which is preferably arranged orthogonally relative to a first plane P1 over which the culture medium 2 extends. The sensing means 6 is advantageously positioned above the Petri dish 4 so as to take a top view of the culture medium 2. The sensing means 6 is for example a CCD camera, notably of the Basler piA2400-17 gm type, which is equipped with a telecentric objective 11. The light source 8 is preferably a collimated illuminator that is able to produce parallel light rays 9 that reach the culture medium 2 orthogonally. The light source 8 comprises a plurality of diodes comprising a range of emission indifferently in the red, green, blue and white.

According to a first embodiment of a first variant illustrated in FIG. 7, the light source 8 is arranged laterally above the Petri dish 4. According to a second embodiment of the first variant illustrated in FIG. 9, the light source 8 is arranged laterally below the Petri dish 4. The light source 8 is associated with an optical focus 8' that allows direct illumination of the Petri dish 4. According to the first embodiment, the light source 8 is associated with a semireflecting mirror 10 inclined at 45° for returning the light rays 9 emitted by the light source 8 to the Petri dish 4. The light source 8 is for example of the Opto Engineering-LTCL 048-W type. The optical focus 8' is for example of the Opto Engineering-LTCL 24 type. In both cases, the telecentric objective 11 is notably of the Opto Engineering-TC23 048 type, comprising a focal field of 46×38.5 mm and a working distance of 134.6 mm.

According to a second embodiment illustrated in FIG. 10, the light source 8 is centered underneath the Petri dish 4 for addressing the light rays 9 emitted by the light source 8 directly onto the Petri dish 4. More particularly, the light source 8 is arranged axially relative to the sensing axis A so as to deliver back-illumination to the Petri dish 4. In this case, the light source 8 is for example of the Opto Engineering-LTCL 024-G type, whose emission wavelength is 520 nm, and the telecentric objective 11 is for example of the Edmund Optics-63733 type, comprising a focal field of 8.44×7.07 mm and a working distance of 65 mm.

The sensing means 6, the light source 8 and optionally the semireflecting mirror 10 and the optical focus 8' together form a detecting device 12 that is able to carry out the method of detection 100 of the present invention.

Referring to FIGS. 5, 6, 5a, 6a, 5b, 6b and 8, when the light rays 9 pass through the first inhibition zones $Z_1$ of the culture medium 2 that are free from biological particles 1, the light rays 9 pass through the culture medium 2 without being deflected, in such a way that the image 7 taken by the sensing means 6 reveals a first portion of the image 7 which is light, notably white, and which is of identical conformation to the first inhibition zones $Z_1$. When the light rays 9 pass through a second proliferation zone $Z_2$ comprising biological particles 1, the latter deflect the light rays 9, in such a way that the image 7 taken by the sensing means 6 reveals a second portion of the image 2 which is dark, notably black, and which is of identical conformation to the second proliferation zones $Z_2$. It follows from this that at a given observation time, the contrast between a first inhibition zone $Z_1$ and a second proliferation zone $Z_2$ is greater than the same contrast observed with a conventional method of the prior art. It should be noted at this stage of the description that the image 7 illustrated in FIG. 8 was obtained using the detecting device 12 illustrated in FIG. 7, the biological particles being Staphylococcus aureus (ATCC 25923), the chemical agent 3 being ciprofloxacin and the detection time $T_X$ being 18 h.

Figure 11A:
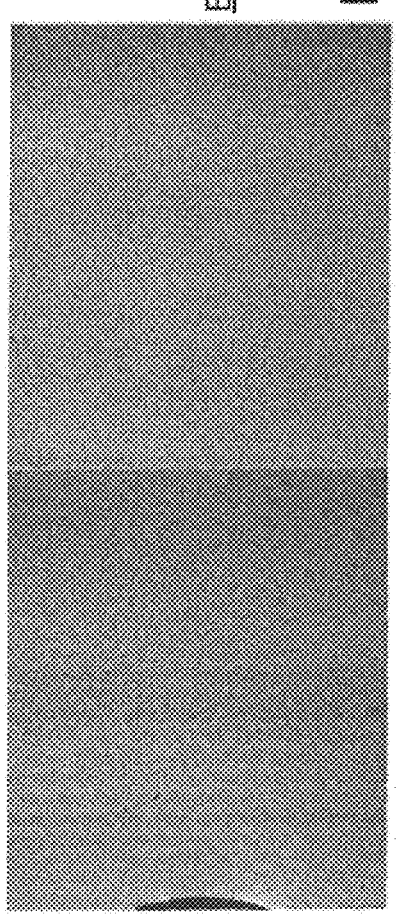
FIGS. 11a, 11b and 11c are images taken by the detecting device illustrated in FIG. 10, of a culture of *Escherichia coli* (ATCC 35218) in the presence of ampicillin, ampicillin-sulbactam and piperacillin-tazobactam, respectively, at a measurement time $T_1$ of two hours.
Figure 11B:
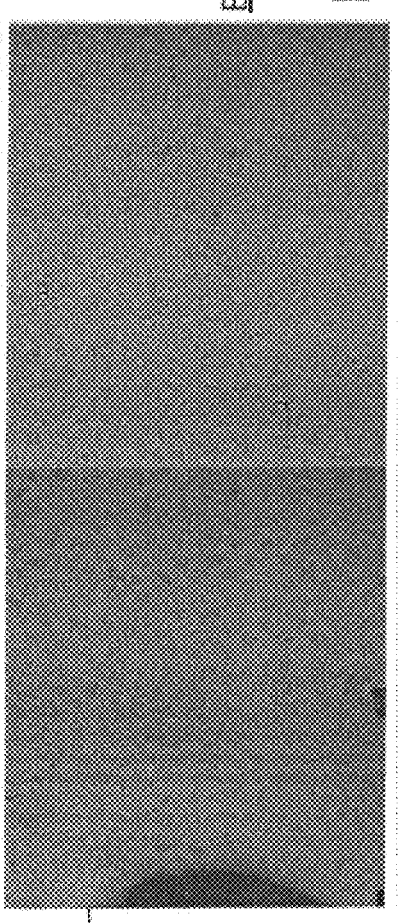
Figure 11C:
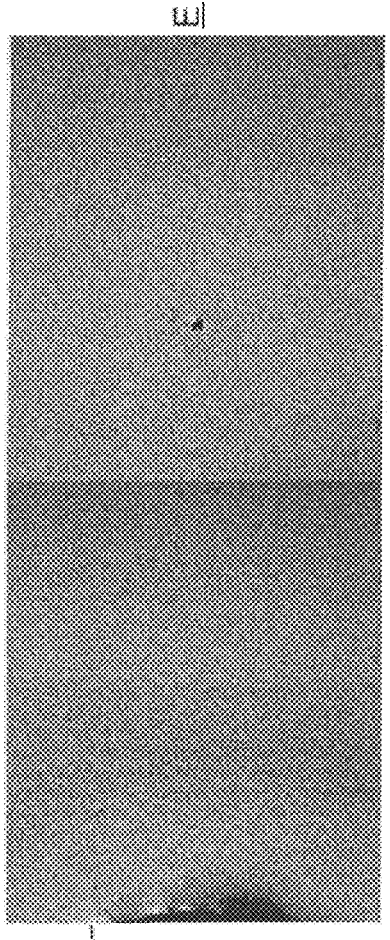
Figure 12A:
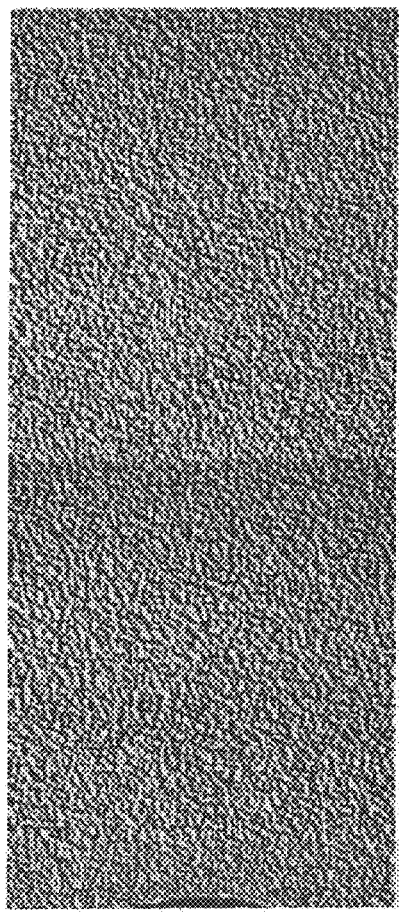
FIGS. 12a, 12b and 12c are images taken by the detecting device illustrated in FIG. 10, of a culture of *Escherichia coli* (ATCC 35218) in the presence of ampicillin, ampicillin-sulbactam and piperacillin-tazobactam, respectively, at a measurement time $T_1$ of four hours.
Figure 12B:
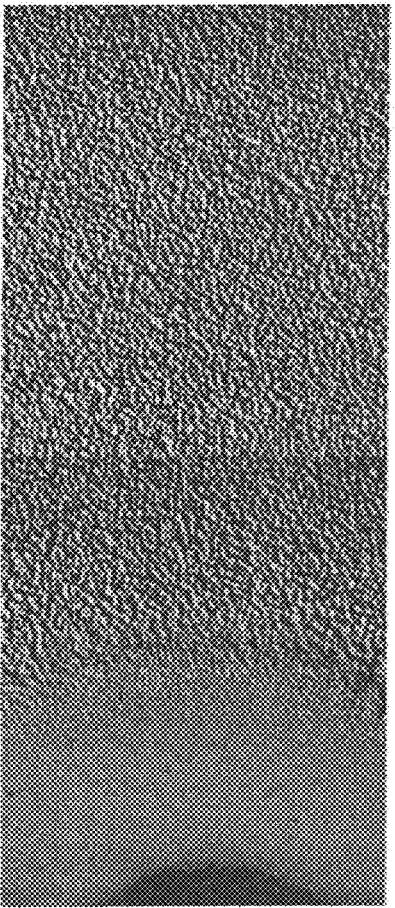
Figure 12C:
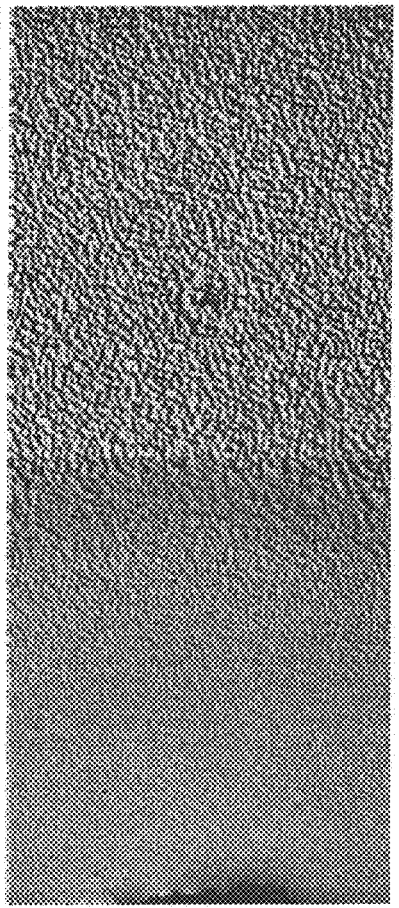
Figure 14A:
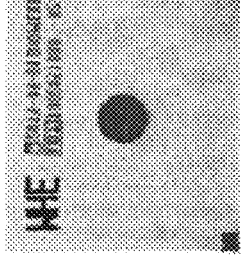
FIGS. 14a, 14b, 14c, 14d, 14e and 14f are images taken by the detecting device illustrated in FIG. 9, of a culture of *Escherichia coli* (ATCC 35218) in the presence of ampicillin at a measurement time $T_1$ of zero hour, two hours, four hours, six hours, eight hours and twenty-four hours, respectively.
Figure 14B:
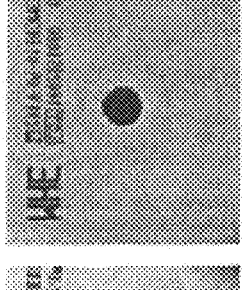
Figure 14C:
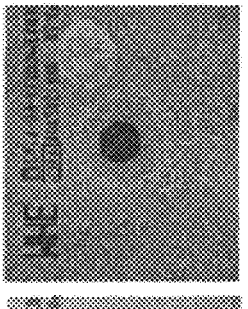
Figure 14D:
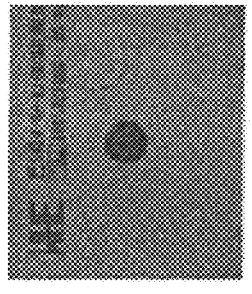
Figure 14E:
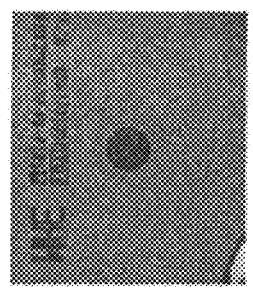
Figure 14F:
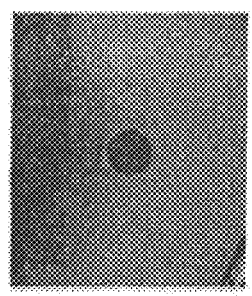
Figure 15A:
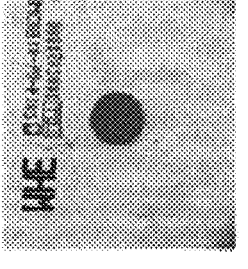
FIGS. 15a, 15b, 15c, 15d, 15e and 15f are images taken by the detecting device illustrated in FIG. 9, of a culture of *Escherichia coli* (ATCC 35218) in the presence of ampicillin-sulbactam at a measurement time $T_1$ of zero hour, two hours, four hours, six hours, eight hours and twenty-four hours, respectively.
Figure 15B:
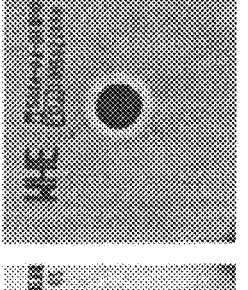
Figure 15C:
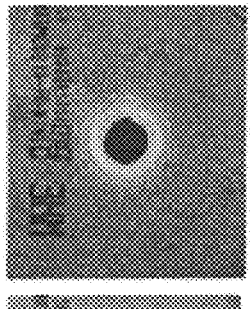
Figure 15D:
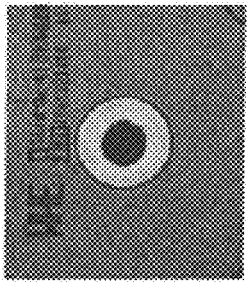
Figure 15E:
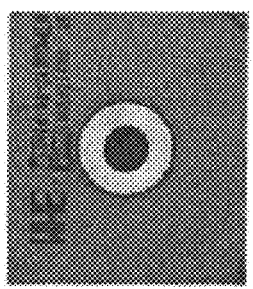
Figure 15F:
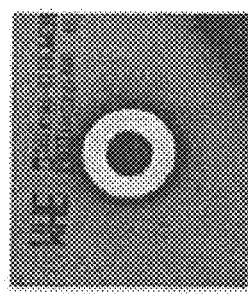
Figure 16A:
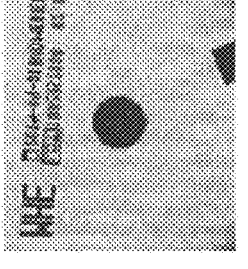
Figure 16B:
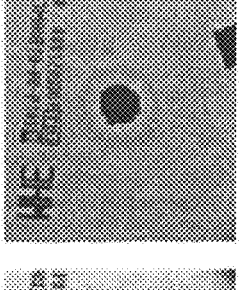
Figure 16C:
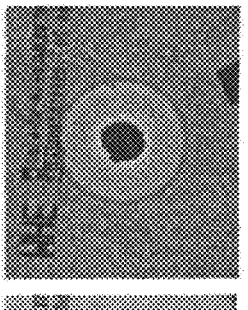
Figure 16D:
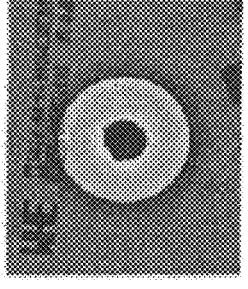
Figure 16E:
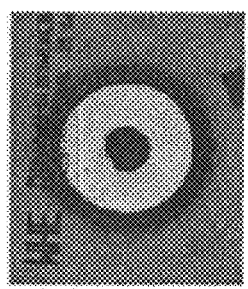
Figure 16F:
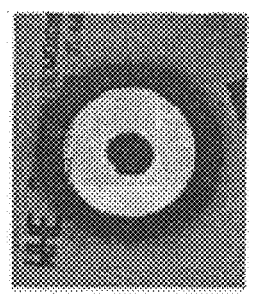

Referring to FIGS. 11a, 11b and 11c, which are images 7 of a culture of Escherichia coli (ATCC 35218) in the presence of ampicillin, ampicillin-sulbactam and piperacillin-tazobactam, respectively, at a measurement time $T_1$ of two hours, and FIGS. 12a, 12b and 12c, which are images 7 of a culture of Escherichia coli (ATCC 35218) in the presence of ampicillin, ampicillin-sulbactam and piperacillin-tazobactam, respectively, at a measurement time $T_1$ of four hours, as well as FIGS. 13a and 13b, which are images 7 of a culture of Escherichia coli (ATCC 25922) in the presence of ampicillin, at a measurement time $T_1$ of two hours and four hours respectively, said images 7 are partial images of the Petri dish 4 consisting of a strip 13 that is radial from the latter, the strip 13 extending between the receiving zone R and a peripheral end E of the Petri dish 4. In such a case, the method of detection 100 is a method of detection by micro-ombroscopy, which offers the advantage of giving better resolution and quicker detection of the first inhibition zone $Z_1$. Thus, in FIGS. 12b, 12c and 13b, the first inhibition zone $Z_1$ is identifiable at a detection time $T_X$ of four hours, or in FIGS. 11b, 11c and 13a to a detection time $T_X$ of two hours. The result is a reliable and definite response regarding the sensitivity of Escherichia coli (ATCC 35218) to the ampicillin-sulbactam mixture and to the piperacillin-tazobactam mixture, regarding the resistance of Escherichia coli (ATCC 35218) to ampicillin with a detection time $T_X$ of four hours. The result is a reliable and definite response regarding the sensitivity of Escherichia coli (ATCC 25922) to ampicillin with a detection time $T_X$ of two hours, said response being comparable to a reference method of the prior art, such as a method of naked-eye observation, but in a much shorter detection time.

Referring to FIGS. 14a, 14b, 14c, 14d, 14e and 14f, which are images 7 of a culture of Escherichia coli (ATCC 35218) in the presence of ampicillin at a measurement time $T_1$ of zero hour, two hours, four hours, six hours, eight hours and twenty-four hours, respectively, it is noticeable that a reliable and definite response of the resistance of Escherichia coli (ATCC 35218) to ampicillin is identifiable starting from four hours. In fact, no inhibition zone is detected starting from four hours, and this is reliable and repeatable over time.

Referring to FIGS. 15a, 15b, 15c, 15d, 15e and 15f, which are images 7 of a culture of Escherichia coli (ATCC 35218) in the presence of ampicillin-sulbactam at a measurement time T1 of zero hour, two hours, four hours, six hours, eight hours and twenty-four hours, respectively, it is noticeable that a reliable and definite response of the sensitivity of Escherichia coli (ATCC 35218) to the ampicillin-sulbactam mixture is identifiable starting from four hours. In fact, the inhibition zone detected starting from four hours has a stable diameter that can be measured repeatably over time.

Referring to FIGS. 16a, 16b, 16c, 16d, 16e and 16f, which are images 7 of a culture of Escherichia coli (ATCC 35218) in the presence of piperacillin-tazobactam at a measurement time $T_1$ of zero hour, two hours, four hours, six hours, eight hours and twenty-four hours, respectively, it is noticeable that a reliable and definite response of the sensitivity of Escherichia coli (ATCC 35218) to the ampicillin-sulbactam mixture is identifiable starting from four hours. In fact, the inhibition zone detected starting from four hours has a stable diameter that can be measured repeatably over time. The examples in FIGS. 14 to 16 show the benefits of using ombroscopy for detecting inhibition zones, which demonstrates the advantage of using ombroscopy in this method, more particularly of using a telecentric objective, preferably combined with a collimated illuminator.

Referring once again to FIG. 2, the aforementioned responses of the various biological particles 1 to the chemicals 3 are obtained from the method of detection 100 of the present invention, which advantageously comprises a fifth step 105 of processing the images 7 obtained by the detecting device 12 of the present invention. The fifth processing step 105 is carried out by employing calculating means 14 configured for executing this step and comprising for example means for image analysis and processing, the calculating means 14 forming part of a processor that is comprised by the detecting device 12.

According to a first approach for the fifth processing step 105, the latter comprises for example Gaussian filtering of the images 7, acquisition of respective profiles of the images and derivation of said profiles.

According to a second approach for the fifth processing step 105, the latter comprises for example localization of the receiving zone R, setting a high dynamic range of the image, median filtering of the latter, acquisition of profiles by rotating the image about the receiving zone R, derivation of said profiles, and calculation of a mean value of profiles to determine the presence or absence of a first inhibition zone $Z_1$ within each of the images 7.

According to one or other of the aforementioned approaches, the method of detection 100 makes it possible to determine reaction kinetics of inhibition, representing the diameter D of the first inhibition zone $Z_1$ as a function of the time t, said kinetics being illustrated in FIGS. 17 and 18. In FIG. 17, curves $C'_1$, $C'_2$, $C'_3$ respectively illustrate the kinetics of the reactions of inhibition in FIGS. 14a to 14f, FIGS. 15a to 15f and FIGS. 16a to 16f. In FIG. 18, curve $C_2$ illustrates reaction kinetics of inhibition of Escherichia coli (ATCC 35218) in the presence of the antibiotic ampicillin-sulbactam, relative to a reference threshold BP for enterobacteria with respect to this antibiotic. After six hours, the measured diameter D is greater than the specified reference threshold BP. As a result, this strain is considered to be sensitive to this antibiotic.

A third approach of the fifth processing step 105 is illustrated in FIGS. 19 to 30.

In FIG. 19, the fifth processing step 105 comprises a second phase $X_2$ of taking a control photograph 7' of a ruler 15 arranged on the culture medium 2 contained in the Petri dish 4, the second phase $X_2$ also being carried out by the detecting device 12. Then the fifth processing step 105 comprises a third phase $X_3$ of superimposing the image 7 and the control photograph 7' and more particularly of their respective receiving zone R to form a normed representation 7" of the culture medium 2.

In FIG. 20, the fifth processing step 105 comprises a fourth phase $X_4$ of localization of a reference mark 16 of the ruler 15. In the example shown, the reference mark 16 is the indication "256" on the ruler 15, and the reference mark 16 may consist of some other and relatively any indication. The reference mark 16 comprises Cartesian coordinates $X_{256}$ and $Y_{268}$.

In FIGS. 21 to 25, the fifth processing step 105 comprises a fifth phase $X_5$ of processing the normed representation 7".

Figure 21:
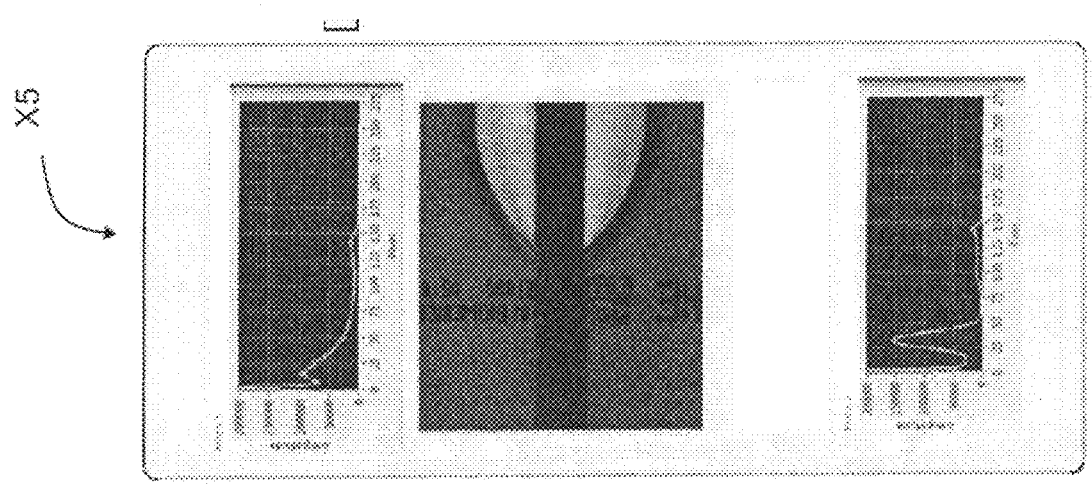

In FIG. 21, the fifth phase $X_5$ comprises at least one smoothing operation for homogenizing the normed representation 7". Said smoothing operation is for example carried out starting from Gaussian filtering of the normed representation 7". Preferably, the smoothing operation is carried out several times, notably seven times.

Figure 22:
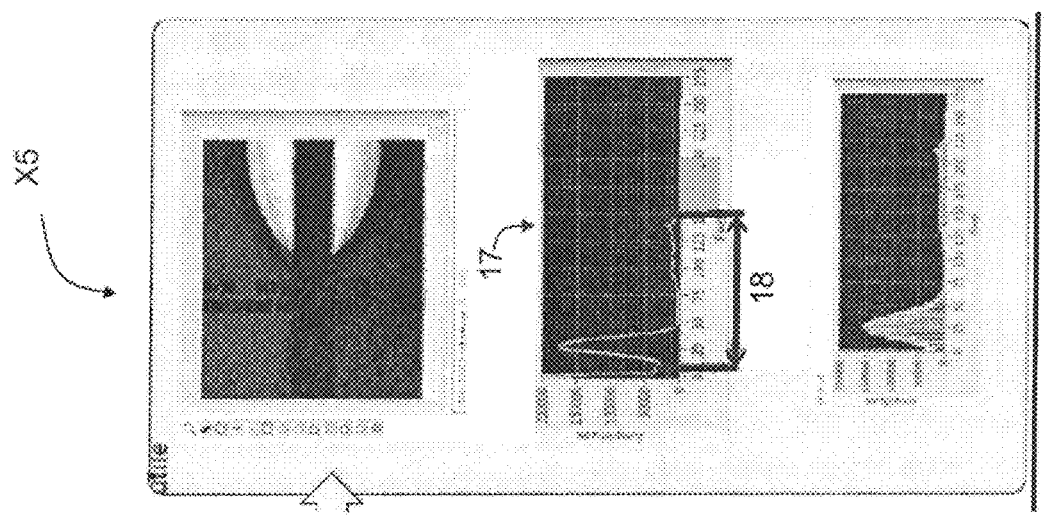

In FIG. 22, the fifth phase $X_5$ comprises at least one operation of stretching the dynamics of the pixel intensity of the normed representation 7" to form a histogram 17 of contrast of the normed representation 7", the contrast being considered between dark pixels and light pixels of the normed representation 7". This results in determination of the useful dynamics 18 of the normed representation 7".

Figure 23:
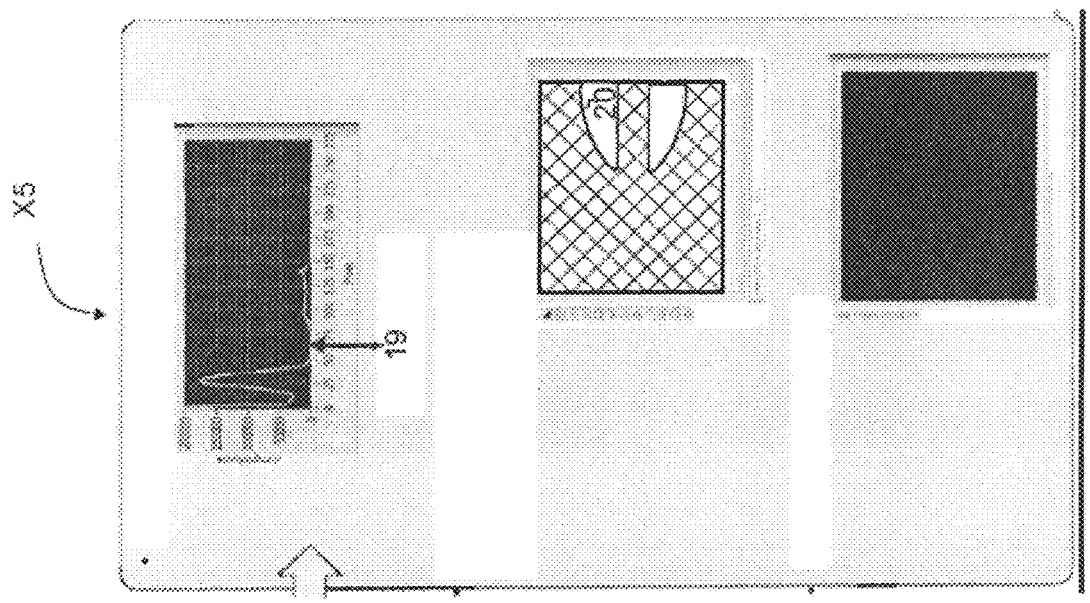

In FIG. 23, the fifth phase $X_5$ comprises at least one thresholding operation of the normed representation 7", which comprises for example detection of a threshold 19 and determination of a contour 20 from digitization of the normed representation 7".

Figure 24:
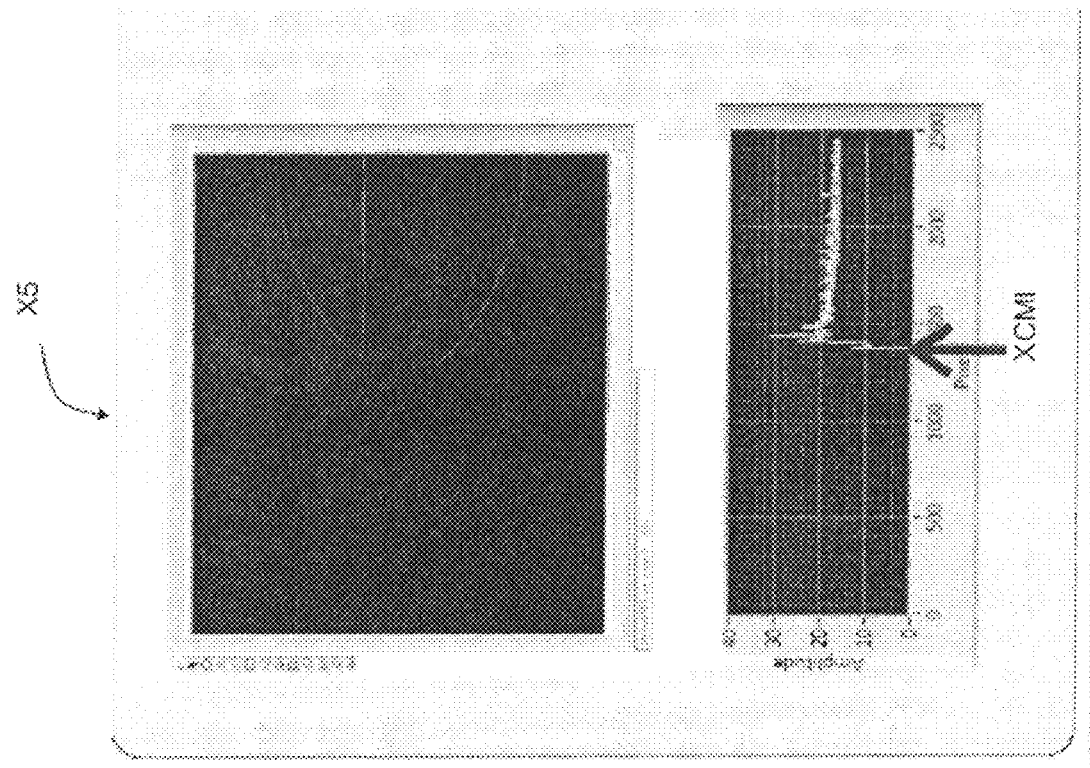

In FIG. 24, the fifth phase $X_5$ comprises at least one operation of estimating a minimum inhibitory concentration, commonly known by the acronym MIC, based on determination of the abscissa of the referenced minimum inhibitory concentration $X_{MIC}$.

Figure 25:
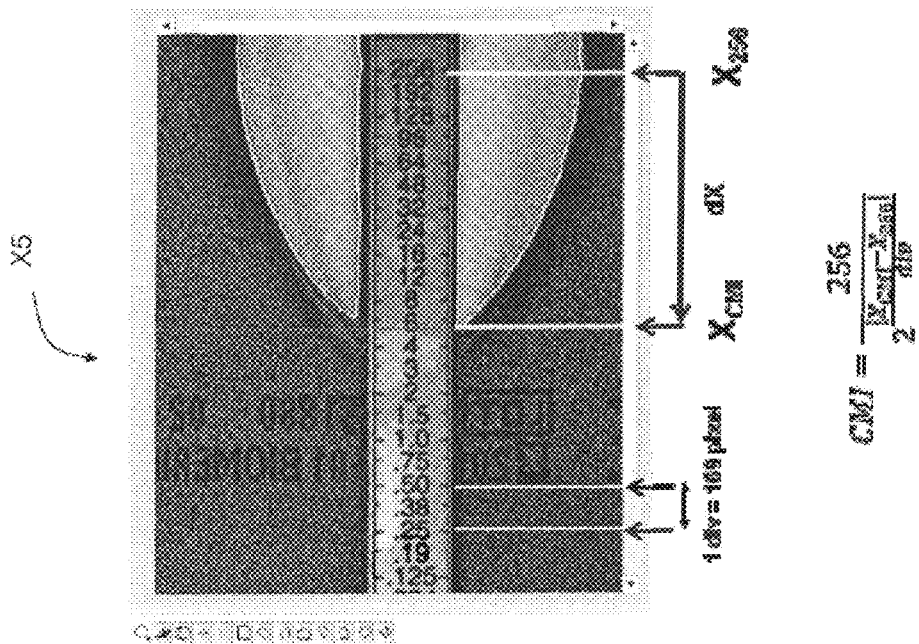

In FIG. 25, the fifth phase $X_5$ comprises at least one operation of calculating the minimum inhibitory concentration MIC from the following relation [1]:

$$CMI = \frac{256}{2^{\frac{|X_{CMi}-X_{256}|}{div}}} \qquad [1]$$

with a constant "div" that corresponds to a number of pixels between two graduations of the ruler 15 separated by a factor 2. The constant "div" is for example equal to one hundred and sixty-nine pixels.

These arrangements, taken together, are such that the minimum inhibitory concentration MIC, which is the concentration of chemical agent 3 starting from which the first inhibition zone $Z_1$ appears, is determined accurately, reliably, repeatably and with a reliable response time which is short, notably less than or equal to eight hours.

Figure 27:
Figure 26:
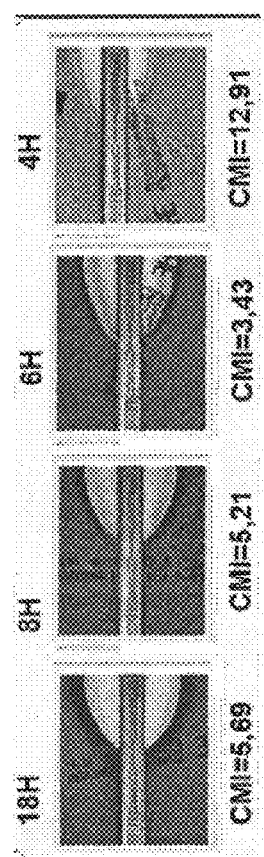

FIGS. 26 and 27 show normed representations 7" of a culture of Escherichia coli (ATCC 25922) in the presence of ampicillin, for which it is noticeable that starting from six hours, the calculated minimum concentration MIC makes it possible to characterize the response of Escherichia coli (ATCC 25922) as sensitive to ampicillin.

Figure 28:
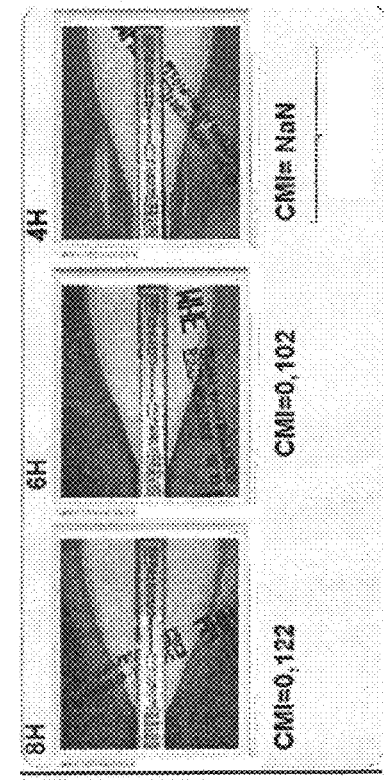

FIG. 28 shows the normed representation 7" of a culture of Staphylococcus aureus (ATCC 25923) in the presence of ampicillin, for which it is noticeable that starting from six hours, the calculated minimum concentration MIC makes it possible to characterize the response of Staphylococcus aureus (ATCC 25923) as sensitive to ampicillin.

Figure 29:
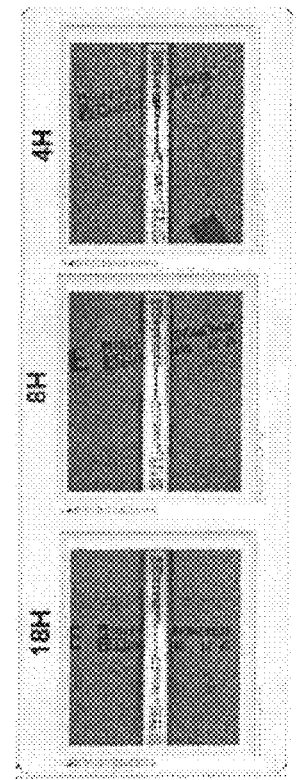

FIG. 29 shows the normed representation 7" of a culture of Escherichia coli (ATCC 35218) in the presence of ampicillin, for which it is noticeable that Escherichia coli (ATCC 35218) is resistant to ampicillin based on absence of a first inhibition zone $Z_1$.

Figure 30:
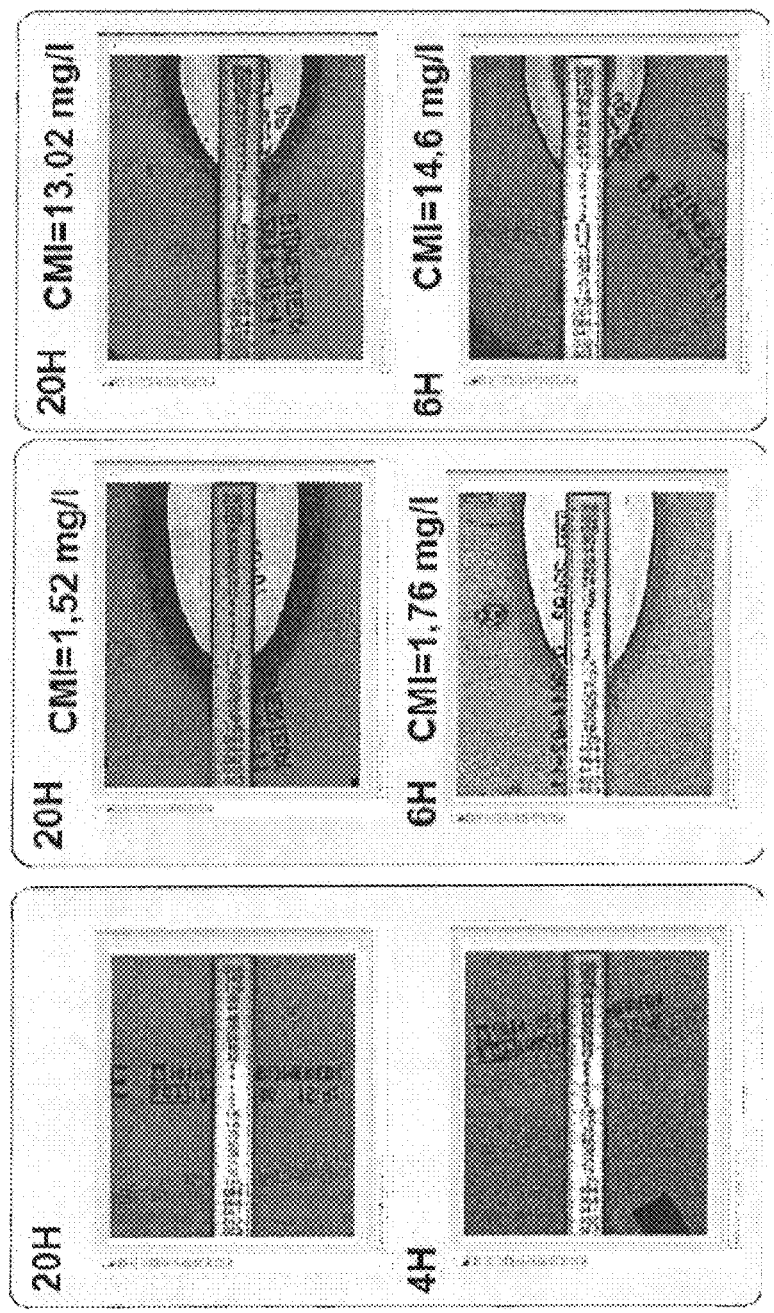

FIG. 30 shows successively in columns from left to right, the normed representations 7" of a culture of Escherichia coli (ATCC 35218) in the presence of ampicillin, a mixture of piperacillin and tazobactam, and a mixture of ampicillin and sulbactam, respectively, for which it is noticeable that Escherichia coli (ATCC 35218) is both resistant to ampicillin, sensitive to the mixture of piperacillin and tazobactam and intermediate to the mixture of ampicillin and sulbactam, according to EUCAST (European Committee on Antimicrobial Susceptibility Testing).

These arrangements, taken together, are such that by employing the method of detection 100 of the present invention, a first inhibition zone $Z_1$ is reliably detectable four hours after the biological particles 1 and the chemical agent 3 are brought together, in the case of sensitivity of the former to the latter.

FIGS. 31a, 31b, 31c are images taken by the detecting device illustrated in FIG. 9, of a suspension of Staphylococcus aureus on a chromogenic culture medium ChromoID™ MRSA Smart opaque (bioMérieux, Ref. 413050). Seeding is performed by flooding with a solution calibrated at 0.5 McFarland; an Etest® strip (bioMerieux) containing a concentration gradient of cefoxitin is then arranged on the surface of the medium. The medium is incubated at 37° C. and images are captured at a respective measurement time $T_1$ of four hours, 31a, five hours, 31b and finally twenty hours, 31c.

FIGS. 32a, 32b, 32c are images taken by the detecting device illustrated in FIG. 9, of a suspension of *Staphylococcus aureus* on a chromogenic culture medium ChromoID™ MRSA transparent (bioMérieux, Ref. 43451). Seeding is performed by flooding with a solution calibrated at 0.5 McFarland; an Etest® strip (bioMérieux) containing a concentration gradient of cefoxitin is then arranged on the surface of the medium. The medium is incubated at 37° C. and images are captured at a respective measurement time $T_1$ of four hours, 32a, five hours, 32b, and twenty hours, 32c.

FIGS. 33a, 33b, 33c are images taken by the detecting device illustrated in FIG. 9, of a suspension of *Staphylococcus epidermidis* on a chromogenic culture medium CPS® ID 3 (CPS3) (bioMérieux, Ref. 43541). Seeding is performed by flooding with a solution calibrated at 0.5 McFarland; an Etest® strip (bioMérieux) containing a concentration gradient of gentamicin is then arranged on the surface of the medium. The medium is incubated at 37° C. and images are captured at a respective measurement time $T_1$ of four hours, 33a, five hours, 33b, and six hours, 33c.

FIGS. 34a, 34b, 34c are images taken by the detecting device illustrated in FIG. 9, of a suspension of *Staphylococcus aureus* on a chromogenic culture medium CPS® ID 3 (CPS3) (bioMérieux, Ref. 43541). Seeding is performed by flooding with a solution calibrated at 0.5 McFarland; an Etest® strip (bioMérieux) containing a concentration gradient of gentamicin is then arranged on the surface of the medium. The medium is incubated at 35° C. and images are captured at a respective measurement time $T_1$ of four hours, 34a, five hours, 34b, and six hours, 34c.

The values of minimum inhibitory concentration obtained from FIGS. 31 to 34 starting from 4 hours meet the EUCAST recommendations for the corresponding microorganisms, for conventional reading after twenty hours of incubation. It is also noticeable that the values of minimum inhibitory concentration readable starting from four hours in FIGS. 31a, 32a, 33a and 34a are also similar to the values readable starting from five hours in FIGS. 31b, 32b, 33b and 34b. Moreover, the inhibition zones observable are sufficiently stable and repeatable so that the values at six hours, 33c, 34c and twenty hours 31c, 32c are also similar. Accordingly, the advantage in using ombroscopy, more particularly using a telecentric objective preferably coupled to a collimated illuminator, is demonstrated for reading at less than eight hours, or even at less than six hours, preferably at four hours, of a value of minimum inhibitory concentration that is reliable and repeatable, for all types of culture media, notably chromogenic media. The advantage of this technique has also been demonstrated for imaging on opaque media, FIGS. 31a, 31b, 31c, these media being known to be difficult to analyze. Thus, the opacity of the medium increases the diffusion of any illumination through the agar and thus reduces the contrast of the image captured. Thus, it can be seen that all the images captured in FIGS. 31 to 34 have sufficiently high contrast between the zones of bacterial growth and the inhibition zones so that the image is easy to analyze using calculating means comprising for example means for image analysis and processing, the calculating means forming part of a processor comprised by the detecting device 12.

Finally, these assays performed on two different types of antibiotics, namely a bactericide (cefoxitin) and a bacteriostatic (gentamicin), can also show the capacity of the method according to the invention for obtaining an inhibition value quickly, starting from four hours and in less than eight hours, and moreover repeatably over time. The influence of the refractive index of the chemical agent on the image captured is also limited by the use of ombroscopy, more particularly using a telecentric objective preferably coupled to a collimated illuminator. Another advantage of ombroscopy used with identifying media such as chromogenic media is also the capacity for simultaneous execution of a step for identifying the biological particles, typically of the type of microorganisms that are present, and of a step of estimating a value of minimum inhibitory concentration, based on a single culture medium and a single image acquisition step.

FIGS. 35a, 35b, 35c are images captured by different detecting devices. FIG. 35a is obtained by a system described in international patent application WO 2012/152768 (reference SIU). The illumination used for image acquisition is low annular illumination, consisting of four linear arrays of ten RGB LEDs arranged perpendicular to the culture medium and oriented toward the surface of the culture medium at an angle of 45°. The four linear arrays are distributed regularly at 90° around the medium. The sensor used for image acquisition is a CMOS sensor of 5 megapixels, each pixel representing an area of 3.45 μm by 3.45 μm. A black background is arranged under the culture medium for image acquisition. Only channel R (red) of the images captured is shown. FIG. 35b is obtained using "Bio-System Incubator" apparatus marketed by the company ADVENCIS and described in international patent application WO 2013/110734 (reference Advencis), consisting of a scanner having linear illumination by reflection and a linear camera. FIG. 35c is obtained using the device illustrated in FIG. 9 (reference OMBRO). For each of these images, a Mueller Hinton E culture medium (bioMérieux MHE) is seeded by flooding with a suspension of *Escherichia coli* calibrated at 0.5 McFarland. An Etest® strip (bioMérleux) having a gentamicin gradient is placed on the surface of each medium. Each of the images is obtained at a time of measurement and incubation at 37° C. $T_1$ of six hours. In order to quantify the contrast difference obtained, a zone A is defined, visible in FIG. 35c, whose width is delimited by the graduations "192" and "256" of each strip along a Y axis and with a length of 50 mm on the X axis. This zone is perpendicular to the strip, which then extends parallel to the Y axis. A profile along X is then obtained by finding, for each position in X, the average of the gray values of the pixels along Y in zone A. The profiles thus obtained are shown in FIG. 36 for each of the image acquisition devices with the respective references SIU, ADVENCIS and OMBRO.

Thus, FIG. 36 is a schematic illustration of three gray level profiles (GL, 8-bit coded) observed on images captured by the three detecting devices: "SIU" for FIG. 35a, "Advencis" for FIG. 35b and "OMBRO" for FIG. 35c. The transition between the bacterial lawn, the growth zone, and the inhibition zone, as well as between the inhibition zone and the Etest® strip, can be seen on each profile in FIG. 36. In order to estimate the contrast obtained with each device, Imax denotes the maximum gray value observed in the zone of the bacterial lawn and imin denotes the minimum gray value observed in the inhibition zone. Thus, the contrast is calculated from the equation:

$$\text{Contrast} = (I\text{max} - I\text{min})/(I\text{max} + I\text{min})$$

Table 1 below gives the results for contrast for the three profiles:

TABLE 1

|  | Ombro | SIU | Advencis |
| --- | --- | --- | --- |
| lmin | 85 | 118 | 47 |
| lmax | 190 | 139 | 54 |
| Contraste | 38.18% | 8.17% | 6.93% |
| Min | 85 | 118 | 47 |
| Max | 190 | 139 | 54 |
| Contrast | 38.18% | 8.17% | 6.93% |

The results for contrast for the three profiles demonstrate that the OMBRO ombroscopy device, more particularly using a telecentric objective preferably coupled to a collimated illuminator, gives a contrast value of 38.18%, well above the other techniques, and starting from six hours of incubation. Moreover, the value of minimum inhibitory concentration observed certainly meets the recommendations of the regulatory agencies for this antibiotic/microorganism pair.

FIGS. 37a, 37b, 37c are images captured by a detecting device, "SIU", of a suspension of *Escherichia coli* (ATCC "American Type Culture Collection" 25922) on a Mueller Hinton E culture medium (bioMérieux MHE), in the presence of gentamicin after incubation at a measurement time $T_1$ of four hours, six hours and twenty-four hours, respectively. Only channel R (red) of the images captured is shown.

FIGS. 38a, 38b, 38c are images captured by a detecting device, by ombroscopy according to FIG. 9, of a suspension of *Escherichia coli* (ATCC 25922) on a Mueller Hinton E culture medium (bioMérieux MHE), in the presence of gentamicin after incubation at a measurement time $T_1$ of three hours thirty minutes, six hours and twenty-four hours, respectively.

FIGS. 39a and 39b are schematic illustrations of three gray level profiles (GL, 8-bit coded) observed on images captured at each measurement time for each of the devices used for obtaining FIGS. 37a, 37b and 37c and 38a, 38b, 38c.

Table 2 below gives the results for contrast for the three profiles at each incubation time:

TABLE 2

| 3H30 | Ombro | SIU | 4 H |
| --- | --- | --- | --- |
| lmin | 70 | 87 |  |
| lmax | 165 | 87 |  |
| Contraste | 40.43% | 0.00% |  |
| 6 H | Ombro | SIU | 6 H |
| lmin | 70 | 87 |  |
| lmax | 180 | 95 |  |
| Contraste | 44.00% | 4.40% |  |
| 24 H | Ombro | SIU | 24 H |
| lmin | 70 | 87 |  |
| lmax | 190 | 110 |  |
| Contraste | 46.15% | 11.68% |  |

[Contraste = Contrast]

Thus, it can be seen that ombroscopy generates more contrast than the SIU imaging device. In fact, starting from three hours thirty minutes, the level of contrast observed is more than 40%, whereas even after four hours of incubation the SIU device does not give any contrast, and therefore no inhibition zone can be determined reliably and repeatably. Moreover, even after twenty-four hours of incubation the level of contrast is only 11.68%, which may lead to false determination of a minimum inhibitory concentration and is unacceptable in the clinical decision process involving patients' health. The gray level profiles obtained by ombroscopy, particularly using a telecentric objective preferably coupled to a collimated illuminator, therefore display far greater contrast, which also allows analysis by calculating means, notably an automated step of measurement 104 and processing 105 that is more reliable and repeatable.

The methods and devices described in the present invention can be implemented by one or more computer programs, which may be presented in various forms, active or inactive, on a single computer or distributed over computer systems. For example, they may be implemented by software comprising instructions capable of implementing the methods of the present invention and described in the form of source code, object code, executable code or any format allowing certain steps of the methods according to the invention to be carried out, notably the measurement step 104 and/or the processing step 105. All these computer programs may be stored on a computer-readable storage medium, which includes the storage media and corresponding signals, in compressed or decompressed form.

The term computer refers to any electronic device comprising a processor, such as a central processing unit (CPU), a dedicated processor or a microcontroller. A computer is able to receive data (one or more inputs), perform a sequence of predetermined steps on said data, and produce a result in the form of data or signals (one or more outputs). Depending on the context, the term computer may signify a processor in particular or more generally a processor associated with an assembly of interconnected elements contained in a single casing.

The term storage medium or computer-readable storage medium refers to any means for containing, storing, communicating, distributing, or transporting the computer program for it to be used by or in relation with a computer or any means for executing said program. The computer-readable storage medium may be, nonexhaustively, an electronic, magnetic, optical, electromagnetic, infrared or semiconductor system as well as an apparatus, device or means for propagating said program. More-specific, nonlimiting examples of storage media are a floppy disk, a CD-ROM, random access memory (RAM), read-only memory (ROM), erasable programmable read-only memory (EPROM or FLASH storage), an optical fiber, or any electrical connection comprising one or more cables.

The invention claimed is:

1. A method for detecting the presence or absence of at least one first inhibition zone comprised by a culture of biological particles on a culture medium in the presence of a chemical agent, said method of detection comprising
 a first step of seeding the culture medium with the biological particles,
 a second step in which the culture medium receives a support impregnated with the chemical agent, and
 a third step of incubation of the culture medium, wherein the method of detection comprises
   a fourth step of measurement comprising:
    a first phase of taking an image of the culture medium by ombroscopy so as to generate a two-dimensional intensity image of the culture medium in which the first inhibition zone is darker than a proliferation zone of the biological particles, an analysis of the two-dimensional intensity image in which the presence of the first inhibition zone is detected, measuring a diameter of the first inhibition zone and a distance between the impregnated support and an edge of the first inhibition zone, and at least one operation of estimating a minimum inhibitory concentration based on determination of an abscissa of the referenced minimum inhibitory concentration, to determine sensitivity of the biological particles to the chemical agent; wherein the first phase, the analysis, the measuring and the at least one operation of estimating are implemented by a detecting device including a processor comprising a calculating means configured to implement the fourth step of measurement.

2. The method of detection as claimed in claim 1, wherein the method of detection comprises a fifth processing step, which comprises a second phase of taking a control photograph of the culture medium.

3. The method of detection as claimed in claim 2, wherein the control photograph is a photograph of a ruler arranged on the culture medium.

4. The method of detection as claimed in claim 2, wherein the method of detection comprises a third phase of superimposing the image and the control photograph to form a normed representation.

5. The method of detection as claimed in claim 2, wherein the fifth processing step comprises a fourth phase of localization of a reference of the ruler.

6. The method of detection as claimed in claim 2, wherein the fifth processing step comprises a fifth phase of processing the normed representation.

7. The method of detection as claimed in claim 6, wherein the fifth phase comprises at least one smoothing operation for homogenizing the normed representation.

8. The method of detection as claimed in claim 6, wherein the fifth phase comprises at least one operation of dynamic stretching of the normed representation, which comprises spreading of the normed representation to form a histogram of a contrast of the normed representation.

9. The method of detection as claimed in claim 6, wherein the fifth phase comprises at least one thresholding operation of the normed representation, which comprises detection of a threshold and determination of a contour of the normed representation.

10. The method of detection as claimed in claim 2, wherein the first phase of taking the image and the second phase of taking the control photograph are phases that are performed continuously.

11. The method of detection as claimed in claim 2, wherein the first phase of taking the image and the second phase of taking the control photograph are phases that are performed with a defined time lapse.

12. The method of detection as claimed in claim 1, wherein the first inhibition zone is present, and the presence of the first inhibition zone is detectable within four hours after the biological particles and the chemical agent are brought together.

13. The method of detection as claimed in claim 12, wherein the estimated minimum inhibitory concentration is obtained within a period of four to eight hours after the biological particles and the chemical agent are brought together.

* * * * *